United States Patent
Wortman

(10) Patent No.: US 10,492,691 B2
(45) Date of Patent: Dec. 3, 2019

(54) SYSTEMS AND METHODS FOR TISSUE STIFFNESS MEASUREMENTS

(71) Applicant: Massachusetts Institute of Technology, Cambridge, MA (US)

(72) Inventor: Tyler D. Wortman, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/253,375

(22) Filed: Aug. 31, 2016

(65) Prior Publication Data

US 2017/0061621 A1 Mar. 2, 2017

Related U.S. Application Data

(60) Provisional application No. 62/212,381, filed on Aug. 31, 2015.

(51) Int. Cl.
| | | |
|---|---|---|
| *G06K 9/00* | | (2006.01) |
| *A61B 5/00* | | (2006.01) |
| *G06T 7/00* | | (2017.01) |

(52) U.S. Cl.
CPC .......... *A61B 5/0077* (2013.01); *A61B 5/0082* (2013.01); *A61B 5/442* (2013.01); *G06T 7/0012* (2013.01); *G06T 7/0016* (2013.01); *G06T 2207/10012* (2013.01); *G06T 2207/10024* (2013.01); *G06T 2207/10028* (2013.01); *G06T 2207/30088* (2013.01)

(58) Field of Classification Search
CPC ... G06T 7/0012; G06T 7/0016; A61B 5/0082; A61B 5/442; A61B 5/0077

USPC ........................................................ 382/128
See application file for complete search history.

(56) References Cited

U.S. PATENT DOCUMENTS

| | | | |
|---|---|---|---|
| 5,146,923 | A | 9/1992 | Dhawan |
| 5,474,070 | A | 12/1995 | Ophir et al. |
| 5,524,636 | A | 6/1996 | Sarvazyan et al. |
| 6,585,647 | B1 | 7/2003 | Winder |
| 7,257,244 | B2 | 8/2007 | Miga |
| 7,415,143 | B2 | 8/2008 | Grichnik |
| 8,045,868 | B2 | 10/2011 | Kuramochi et al. |
| 8,194,952 | B2 | 6/2012 | Mertz et al. |

(Continued)

FOREIGN PATENT DOCUMENTS

| | | |
|---|---|---|
| CN | 103263250 A | 8/2013 |
| WO | 2013148990 A1 | 10/2013 |

(Continued)

OTHER PUBLICATIONS

Kolipaka, Arunark, et al. "Magnetic resonance elastography as a method for the assessment of effective myocardial stiffness throughout the cardiac cycle." Magnetic resonance in medicine 64.3 (Jun. 23, 2010): 862-870.

(Continued)

*Primary Examiner* — Van D Huynh
(74) *Attorney, Agent, or Firm* — McCarter & English, LLP

(57) ABSTRACT

Automated tissue stiffness measurement devices and methods can identify cancerous lesions with high sensitivity and specificity. Systems and methods are presented to measure tissue stiffness using applied force, illumination and imaging techniques. The systems and methods can use structured illumination to characterize a tissue surface.

41 Claims, 33 Drawing Sheets

(56) References Cited

U.S. PATENT DOCUMENTS

| | | | |
|---|---|---|---|
| 8,425,433 | B2 | 4/2013 | Dunn et al. |
| 8,562,546 | B2 | 10/2013 | Shih et al. |
| 8,826,749 | B2 | 9/2014 | Shih et al. |
| 9,125,589 | B2* | 9/2015 | Sornes ............... A61B 5/02007 |
| 9,554,777 | B2 | 1/2017 | Kim et al. |
| 2003/0210811 | A1 | 11/2003 | Dubowsky et al. |
| 2004/0059220 | A1 | 3/2004 | Mourad et al. |
| 2005/0205667 | A1* | 9/2005 | Rowe ................... A61B 5/1171 235/382 |
| 2006/0239547 | A1 | 10/2006 | Robinson et al. |
| 2006/0259102 | A1* | 11/2006 | Slatkine ............... A61B 17/205 607/88 |
| 2007/0263226 | A1* | 11/2007 | Kurtz ................... A61B 5/0059 356/492 |
| 2008/0123927 | A1 | 5/2008 | Miga et al. |
| 2008/0167585 | A1* | 7/2008 | Khen ..................... A61B 18/14 601/6 |
| 2008/0212864 | A1* | 9/2008 | Bornefalk ............ G06K 9/4642 382/132 |
| 2008/0287780 | A1 | 11/2008 | Chase et al. |
| 2009/0216131 | A1* | 8/2009 | Chase .................. A61B 5/0064 600/476 |
| 2009/0326383 | A1* | 12/2009 | Barnes ................. A61B 5/0059 600/476 |
| 2010/0121230 | A1 | 5/2010 | Vogel et al. |
| 2011/0040192 | A1 | 2/2011 | Brenner et al. |
| 2011/0060210 | A1 | 3/2011 | Ehman |
| 2011/0206254 | A1* | 8/2011 | Patwardhan ......... A61B 5/0077 382/128 |
| 2011/0319791 | A1 | 12/2011 | Harry et al. |
| 2012/0172685 | A1 | 7/2012 | Gilbert |
| 2013/0023966 | A1* | 1/2013 | Depfenhart .......... A61B 18/203 607/89 |
| 2013/0053701 | A1 | 2/2013 | Wiest et al. |
| 2013/0116637 | A1 | 5/2013 | Weston et al. |
| 2013/0322711 | A1 | 12/2013 | Schultz et al. |
| 2014/0094701 | A1* | 4/2014 | Kwartowitz ......... A61B 8/0875 600/438 |
| 2014/0313303 | A1* | 10/2014 | Davis ....................... A61B 5/68 348/77 |
| 2016/0045115 | A1 | 2/2016 | Chase et al. |

FOREIGN PATENT DOCUMENTS

| | | |
|---|---|---|
| WO | 2015105827 A1 | 7/2015 |
| WO | 2015175837 A1 | 11/2015 |

OTHER PUBLICATIONS

Bloemen, Monica CT, et al. "An objective device for measuring surface roughness of skin and scars." Journal of the American Academy of Dermatology 64.4 (Jan. 2011): 706-715.

Boyer, Gaetan, et al. "Non contact method for in vivo assessment of skin mechanical properties for assessing effect of ageing." Medical engineering & physics 34.2 (Mar. 2012): 172-178.

Cheng, H. M., and P. Guitera. "Systematic review of optical coherence tomography usage in the diagnosis and management of basal cell carcinoma." British Journal of Dermatology 173.6 (Oct. 2015): 1371-1380.

Diridollou, S., et al. "In vivo model of the mechanical properties of the human skin under suction." Skin Research and technology 6.4 (Nov. 2000): 214-221.

Dolicanin, C. B. et al. "Application of finite difference method to study of the phenomenon in the theory of thin plates." Scientific Publications of the State University of Nova Pazar: Appl. Math. Inform. and Mech 2, 1 (May 2010) p. 29-43.

Es'Haghian, Shaghayegh, et al. "Optical palpation in vivo: imaging human skin lesions using mechanical contrast." Journal of biomedical optics 20.1 (Jan. 2015): 016013-016013.

Greenleaf, James F., Mostafa Fatemi, and Michael Insana. "Selected methods for imaging elastic properties of biological tissues." Annual review of biomedical engineering 5.1 (Apr. 2003): 57-78.

Gutkowicz-Krusin, D., et al. "Precision of automatic measurements of pigmented skin lesion parameters with a MelaFind™ multispectral digital dermoscope." Melanoma research 10.6 (Dec. 2000): 563-570.

Kirkpatrick, Sean J., et al. "Imaging the mechanical stiffness of skin lesions by in vivo acousto-optical elastography." Optics express 14.21 (Oct. 2006): 9770-9779.

Krehbiel, Joel David, et al. "Digital image correlation for improved detection of basal cell carcinoma." Experimental Mechanics 50.6 (Jan. 2010): 813-824.

Li, Chunhui, et al. "Determining elastic properties of skin by measuring surface waves from an impulse mechanical stimulus using phase-sensitive optical coherence tomography." Journal of the Royal Society Interface 9.70 (Nov. 2011): 831-841.

Lye, Ian, et al. "Tissue tonometry is a simple, objective measure for pliability of burn scar: is it reliable?." Journal of burn care & research 27.1 (Jan. 2006): 82-85.

Salvi, Joaquim, et al. "A state of the art in structured light patterns for surface profilometry." Pattern recognition 43.8 (Aug. 2010): 2666-2680.

Swaminathan, Vinay, et al. "Mechanical stiffness grades metastatic potential in patient tumor cells and in cancer cell lines." Cancer research 71.15 (Aug. 2011): 5075-5080.

Tilleman, T. R., M. M. Tilleman, and M. H. Neumann. "The elastic properties of cancerous skin: Poisson's ratio and Young's modulus." the Israel Medical Association journal: IMAJ 6.12 (Dec. 2004): 753-755.

Wolf, Joel, et al. "Diagnostic Inaccuracy of Smart Phone Applications for Melanoma Detection." JAMA dermatology 149.4 (Jan. 2013): 422.

Wortman, T. et al. "A Novel Phantom Tissue Model for Skin Elasticity Quantification," poster presentation at the Design of Medical Devices Conference 2016, Minneapolis, MN, Apr. 13, 2016.

Wortman, Tyler, Felicia Hsu, and Alex Slocum. "A Novel Phantom Tissue Model for Skin Elasticity Quantification." Journal of Medical Devices 10.2 (May 12, 2016): 020961.

Xu, Wenwei, et al. "Cell stiffness is a biomarker of the metastatic potential of ovarian cancer cells." PloS one 7.10 (Oct. 2012): e46609.

Sheth et al., A pilot study to determine vitiligo target size using a computer-based image analysis program. J Am Acad Dermatol. Aug. 2015;73(2):342-5.

Wortman, LesionAir: A low-cost tool for automated skin cancer diagnosis mapping. Submitted to the Department of Mechanical Engineering in partial fulfillment of the requirement for the degree of Doctor of Philosophy in Mechanical Engineering at the Massachusetts Institute of Technology. 252 pages, Jun. 2016.

International Search Report and Written Opinion for Application No. PCT/US2016/049722, dated Feb. 1, 2017. 19 pages.

International Preliminary Report on Patentability for Application No. PCT/US2016/049722, dated Mar. 6, 2018. 15 pages.

* cited by examiner

Lesion Segmentation and ABCD quantification using custom algorithm

|  | X | Y | Z | MAG |
| --- | --- | --- | --- | --- |
| Maximum Deviation | 0.0232 | 0.0340 | 0.0261 | 0.0274 |
| Average Deviation | 0.0093 | 0.0172 | 0.0109 | 0.0112 |
| Standard Deviation | 0.0038 | 0.0035 | 0.0040 | 0.0043 |

FIG. 15

SYSTEMS AND METHODS FOR TISSUE STIFFNESS MEASUREMENTS

RELATED APPLICATION

This application claims priority to U.S. Provisional Patent Application No. 62/212,381, filed Aug. 31, 2015, the contents of which is incorporated herein by reference in its entirety.

BACKGROUND OF THE INVENTION

Skin cancer is the most common form of cancer, accounting for one-third of all cancer diagnoses in the United States. This translates to 1 out of 5 Americans developing skin cancer at some point in their lifetime. There are three different primary types of skin cancer based on the type of skin cells that are affected: basal cell carcinoma, squamous cell carcinoma, and melanoma. The non-melanoma cancer types are more frequent, but highly curable. Melanoma, while less common, is much more deadly, causing over 75% of skin cancer deaths. There were an estimated 81,000 new cases and 12,000 deaths resulting from melanoma in 2012. More than 3 million non-melanoma skin cancers and 140,000 melanoma skin cancers afflict people every year in the United States; this translates to one out of every three cancers. Skin cancer incidence and mortality rates are increasing significantly, faster than any other type of cancer. These rates have been steadily rising for both men and women for at least the past 30 years and of the seven most common cancers in the US, melanoma is the only one whose incidence is increasing. Both incidence and mortality rates have a strong positive association with age, are higher for non-Hispanic white males, and most often occur on the trunk and upper extremities. Genetic risk factors and excessive sun exposure are the most common causes of skin cancer.

Increases in incidence have been attributed to expanded skin screenings and the increased detection of tumors with low metastatic potential. Many consider the increased diagnosis rate to arise from evaluation of thinner tumors, but there is also a continued increase in the diagnosis of more fatal, thick (>4 mm) tumors.

A human's skin is made up of three distinct layers: the epidermis, dermis, and hypodermis. Each layer is composed of different types of skin cells. The epidermis, or outermost layer of skin, is made up of squamous cells. Basal cells line the dermal-epidermal junction that separates the two layers. Melanocytes, or melanin producing cells, are spread sporadically within these basal cells. Melanin acts as a filter by using its darker color to absorb UV light. This can protect the hypodermis—which is primarily fatty tissue and vasculature—as well as other internal tissue from dangerous radiation. Cancer can develop when DNA within the skin cells becomes damaged and the body is unable to repair the damage. These damaged cells begin to grow and divide. As the damaged cells multiply, they form a tumor. Since skin cancer generally develops in the epidermis, or outermost layers of skin, a tumor is usually clearly visible. This makes most skin cancers detectable in the early stages.

Identifying skin cancer in its early stages is extremely important to ensure a better chance of survival. Melanoma initially grows horizontally within the epidermis and then after time starts to penetrate into the dermis. Tumor thickness is statistically the most powerful indicator of survival. Probability of survival is inversely related to tumor thickness. Survival rate is greatest for a localized melanoma. Three out of every four melanomas are diagnosed at this stage. If the tumor is less than 0.76 mm, there is a 99% chance for ten-year survival; however this survival percentage drops to less than 50% for a tumor thickness greater than 3 mm. This is due to the increasing potential of melanoma to metastasize as it grows into the dermis making it extremely critical to detect skin cancer in its early stages.

The gold standard for diagnosis has been invasive biopsy and excision, followed by histological and pathological examination. Studies have found that the ratio of biopsies of benign lesions to malignant ones can be as high as 500 to one, while at the same time, one-third of skin cancers are missed. Such statistics show that our current practices have neither specificity nor sensitivity, and a better solution is required.

When a lesion is determined to be cancerous via biopsy, the physician determines the boundaries for excision using a completely subjective visual observation; the only way to verify that the entire lesion was excised is by performing a time-consuming pathology test on the tissue after it has been excised. This method can result in repeat procedures to remove a single lesion, which is inefficient, risks infection, and is cosmetically unappealing.

The effectiveness of the primary treatment method, surgical excision, hasn't changed for decades, but the survival rate has improved—primarily due to earlier detection. It is clear that the single most promising strategy to reduce the mortality rate from melanoma is early detection. Earlier detection also decreases cost. Late stage melanoma is approximately 32 times more expensive than early stage tumors. High costs warrant an increased emphasis on developing effective strategies for early diagnosis.

The key to improving survival rates is early detection. Five-year survival rates for melanoma drop from 98% to 16% and average costs rise as the disease progresses from an early to a late stage. A patient's first point of contact, their primary physician, has significantly lower accuracy when diagnosing skin lesions than dermatologists. With increasing wait times for dermatologists, there is a huge gap in the market for cost-effective detection tool for non-specialists. The healthcare system would save over $260 million per year by reducing unnecessary biopsies and helping patients catch cancer earlier.

Even though early diagnosis almost guarantees survival, the U.S. Preventive Services Task Force concluded there wasn't enough evidence to support routine screening by primary care physicians. This is partially due to the fact there is a considerable debate on who should be screened, who should do the screening, and how often the screening should occur. There are also millions of high-risk melanoma patients with several abnormally appearing lesions. It is impossible to predict which lesions will become cancerous and the excision of all is not practical, requires unnecessary surgery, and does not completely prevent the chance of skin cancer.

Even without routine screening, the majority of patients detect their own melanoma. However, studies have shown that physicians detect melanoma sooner, while it is thinner in its earlier stages. Experience is critical when it comes to detecting early stage melanoma using current methods. The ability to accurately detect melanoma varies widely between individual dermatologists and accuracy drops significantly for non-dermatologists.

SUMMARY OF THE INVENTION

Systems and methods of the present invention relate to the measurement of tissue stiffness. Such measurements may be used in the detection of tissue conditions including, for example, cancerous lesions to provide data that is useful for diagnosis and treatment. Preferred embodiments of the present invention include devices and methods that can analyze one or more tissue characteristics including asymmetry, border (shape or irregularity), color, diameter, elastography, and frequency of blood vessels (also known as vasculature). The devices can measure modification or perturbation of the tissue surface such as a force and/or displacement of tissue and record these measurements along with skin location in a database to compare over time. This data can be sent to a dermatologist for analysis. The device can continually monitor the skin and provide alerts when changes are observed. Skin cancer can be detected utilizing the fact that a changing mole has a 400 times higher relative risk factor for the development of melanoma. The device can look for changes in size, shape, and color utilizing a digital imaging device such as a CCD or CMOS camera and on-board image processing. This process can use one or more algorithms for image analysis.

In accordance with various embodiments, a form of elastography can be implemented to simulate manual palpation and estimate the stiffness of the lesion. The stiffness or elasticity of tissue can be defined as the relationship between force and displacement or stress and strain. The device can use different elastographic methods depending upon application-specific requirements including, but not limited to, desired spatial resolution and cost of implementation. Static, low-resolution methods include tensile, torsion, or indentation techniques. In one embodiment, a constant force is applied to measure the skin surface displacement. In another embodiment, a dynamic, low-resolution method can use a rebound tonometer wherein a mass is bounced off of a lesion and the rebound distance and speed of the mass are measured.

In some embodiments, structured light patterns such as an array of dots or lines, for example, can be employed to produce a dynamic, high-resolution measurement. Structured light may be used to produce 3-D images of skin micro-topography by projecting digital stripes or other patterns onto the skin surface and capturing the positions of the stripes using an imaging device. The systems and methods described herein can use image analysis to process the height differences and generate a 3-D image. Alternatively, a three-dimensional image can be obtained passively using stereoscopy. Multiple cameras with different views are used to measure height differences. By applying a dynamic force, changes in height across the scanned area can be measured and the stiffness can then be calculated.

The systems and methods described herein can exploit the relationship between the frequency of blood vessels or vascularity and the presence of cancerous tissue by using the light absorbed or reflected by the blood vessels. The hemoglobin in blood absorbs light in the blue region of the visible light spectrum; therefore, shining a low-power laser at a wavelength of 400 nm or more generally in a range of 300-450 nm on the skin and measuring the intensity with a receiver can determine vascularity. In such an arrangement, blood vessels can appear as black due to absorption of the light.

In addition to the use of vascularity as a marker to detect a lesion evolving from benign to malignant, the present systems and methods can utilize detection of the increased expression of collagen within the lesion. Levels of collagen can be detected using spectroscopic and optical methods including, but not limited to, Raman, fluorescence, or polarization spectroscopy.

In accordance with various embodiments, the form factor of a tissue stiffness measurement device is structured as hardware and software for use with a mobile wireless device such as a tablet display device or smartphone. This approach is advantageous because it provides a small, portable solution with powerful computational and networking abilities. The mobile device can include an available commercial mobile communication device that connects to a tissue displacement measurement device to measure the elastic response of tissue to displacement which a user can then use to diagnose a condition of the tissue. The mobile measurement device preferably weighs less than 2 kg and can comprise a single handheld unit which is powered by the battery of the tablet or phone. Alternatively, the device can comprise a mobile device such as a tablet or phone connected by a cable or wireless connection to a handheld tissue displacement measurement device. A further embodiment incorporates the components into a single handheld mobile device housing.

In some embodiments, devices of the present invention can be configured for consumers and non-specialists, primary care physicians and nurses, or dermatologists. A consumer-oriented device is useful for those patients that are at a higher risk to develop melanoma. A simple survey utilizing prognostic factors can be used to identify high-risk patients without the need for a dermatologist. Multivariate analysis has shown that there are six risk factors that independently influence the chances of developing malignant melanoma: family history of malignant melanoma; presence of red or blonde hair; presence of marked freckling on the upper back; history of three or more blistering sunburns before age 20; history of three or more years of an outdoor summer job as a youth; and presence of actinic keratosis (scaly or crusty skin lesions). People with one or two of these risk factors have a 3.5 times increased risk, and those with three or more factors have an approximate 20 times increased risk to develop malignant melanoma.

In some embodiments, doctors can use information from the device to monitor their patients through an online database. Alternatively, a tissue stiffness measurement device of various embodiments includes a standalone unit that operates free of a mobile smartphone. The devices and methods disclosed herein implement a tissue stiffness characterization method along with other skin cancer detection techniques in a manner that is cost effective and requires little to no training. The technology completely automates the visual analysis and manual human palpation that occurs when a patient visits the dermatologist—producing greater sensitivity and consistency and turning traditionally subjective tests into objective measurements. Thus, the system includes a computer programmed with a sequence of instructions stored in a memory to execute an automated measurement as described herein.

In addition to skin cancer detection, broader applications of the present invention include diagnosis of other skin diseases, wound mapping, or tissue differentiation for surgery. For example, the systems and devices described herein can be applied to assessment of the severity of an edema. Systems and devices of the present disclosure may also be helpful in planning the excision of a cancerous lesion. Complete removal of the primary skin cancer (basal cell, squamous cell, and melanoma) is the state of the art cure for these primary malignancies. Currently, mapping the extent of a lesion is done visually as there is no commercially available technology used to map a lesion prior to its excision.

There is a very specialized method of skin surgery, called MOHS Micrographic surgery. MOHS attempts to utilize in situ microscope stained sections to determine where cancer has been removed and where it still exists at the edges of the excision. Immediately after tissue is removed, it is processed and placed on microscope slides. The surgeon then maps out where the cancer has been removed and where more cancer needs to be excised.

MOHS is very time consuming and labor intensive. Systems and methods of the present disclosure can be used to accurately map out the lesion, which results in a more accurate determination of excision size and helps achieve smaller margins. Such planning can be done before the surgery thereby reducing the need for MOHS micrographic surgery techniques.

BRIEF DESCRIPTION OF THE DRAWINGS

FIG. 15 depicts the repeatability of an exemplary algorithm in accordance with embodiments of the present invention;

DETAILED DESCRIPTION OF THE INVENTION

Figure 1A:
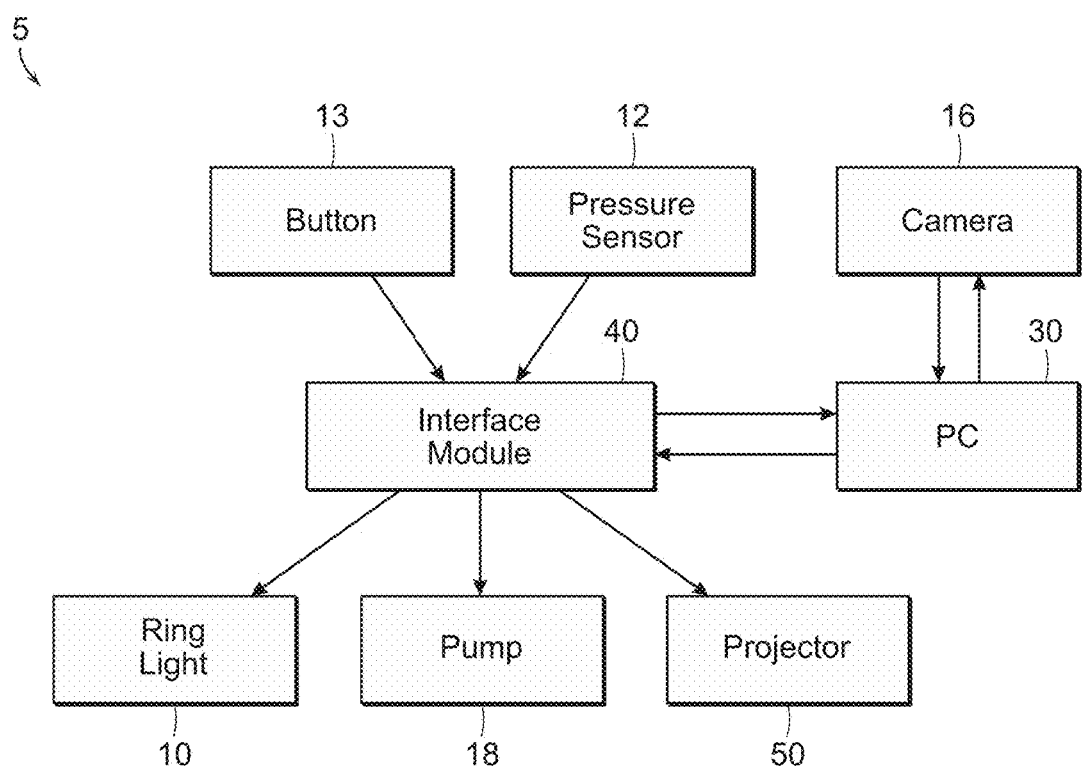
FIG. 1A depicts a schematic view of a control system architecture for a tissue stiffness measurement device according to preferred embodiments.

In this application, reference is made to measurements of stiffness and other properties of skin tissue. However, it will be understood by one skilled in the art that the systems and methods of the present invention may be used to perform the same or similar measurements for any accessible tissue.

According to the World Health Organization, 3 million non-melanoma skin cancers and 132,000 melanoma skin cancers afflict people every year worldwide; as mentioned above, this translates to one out of every three cancers. One out of five Americans will develop skin cancer at some point in his or her life. Identifying early-stage skin cancer before it has metastasized is critical, as prompt excision of the lesion nearly guarantees the patient's recovery. Skin cancer is the only form of cancer that has seen a steady increase in incidence and mortality rates over the past 30 years.

Skin cancer generally develops in the outermost layers of skin, making a possible malignant tumor visible in the early stage when treatment is likely to be most successful. Tissue differentiation is critical for identifying cancerous tissue. It has been challenging to characterize tissue types within the same tissue structure without performing a biopsy. In most clinical settings, practitioners analyze tissue using nothing more than sight and touch. Fidelity is limited due to the resolution and sensitivity constraints of the practitioner; this method is only effective when performed by experienced dermatologists.

The devices and methods disclosed herein conduct automated, non-invasive tissue characterization and diagnosis, which can provide an objective method to rapidly assess the skin of a patient and subsequently map a tumor border for excision.

Advancements in this area have focused on developing optical technologies to assist the dermatologist in diagnosing skin lesions; however, current devices are complex, expensive, and designed to be used by a trained dermatologist only as a means of verifying the initial diagnosis. These methods focus on measuring optical responses, which vary with stimulation and rely on cumbersome, ad-hoc heuristic metrics that have limited reliability and may not work across all clinical populations.

Instead of relying on heuristic methods to gauge cancerous tissue, embodiments of the present invention accurately measure skin stiffness, which is an intrinsic property that changes when tissue becomes cancerous. Automating stiffness measurement increases sensitivity and consistency over existing methods.

While stiffness can be calculated from force and deflection, applying a known force to viscoelastic tissue and measuring deflection accurately is challenging. To obtain deflection, a 3-D model is required. In the past, ultrasound or MRI have been used to quantifiably map the elastic properties of tissue. Unfortunately, the size and costs of such equipment prevent these methods from being adopted in many clinical environments.

A low-cost way to create a 3-D model of a scene is to perform 3-D reconstruction using stereo image processing. In various embodiments, 3-D reconstruction may be performed using stereo matching or structured light. In some embodiments, two or more cameras can be used to capture different views of an object, Stereo matching can algorithmically match up content in a left and right view of a scene similar to how human depth perception works. Feature matching, or correspondence, algorithms can match up content from each of the views. The amount of offset, or disparity, of features is used to determine their depth. Feature-matching provides a sparse reconstruction, while stereo matching creates a dense reconstruction. Dense reconstruction provides depth information for every pixel of the camera, whereas sparse reconstruction only provides depth information for a sample of pixels. By looking at the displacement of content between the left and right views, depth information can be recovered. This process is highly dependent on the characteristics of the tissue being measured to accurately match content, so is more difficult to implement for skin imaging.

Structured light is a technique for 3-D reconstruction in which a light projector casts an image of known geometry onto the tissue surface. In some embodiments, structured light methods can utilize a video projector that scans a visible, UV, or IR wavelength structured pattern through the scene. An algorithm combines the apparent view received by the imaging device with the known geometry of the projected pattern to obtain depth information from the scene. By actively projecting an illumination pattern on the scene, there is no need to rely on features inherent to the scene (like edges, gradients, or texture) so long as the imaging device can see the projected pattern. Structured light can be non-invasive, low cost, low power, accurate, and robust, and can be arranged to allow standard clinical images of the lesion for morphology analysis without additional hardware.

Various pattern encodings can be used in structured light methods, including points, lines, coded binary patterns, color coded stripes, random texture, and more. These patterns can be encoded within one frame (spatially) or across multiple frames (temporally). Spatial encoding uses a single static pattern that allows for dynamic scenes to be captured and provides sparse reconstruction. Temporal encoding has greater redundancy and can be used to acquire dense reconstructions. Differences may exist in speed, bulk, and cost between devices that static and temporal encoding methods.

In some embodiments, a fixed-pattern projector can be used to provide structured light with static encoding. The fixed-pattern projector can use a gobo, or go-between, which is a physical stencil mask that is placed in front of a light source and focused with a lens. A gobo can provide the benefits of structured light, without the bulkiness and cost of projectors. Although static encoding provides sparse reconstruction, skin is fairly continuous without sharp changes in profile and, thus, skin has low spatial frequency. Based on Nyquist sampling theory, sparse reconstruction can be sufficient to describe the scene.

Traditionally, structured light systems have used a video projector to illuminate the skin which adds cost, power requirements, and complexity. As an alternative, a video projector can be used with a fixed projection pattern device placed between an LED and projection optics. This reduces costs, power requirements, and complexity, and enables a handheld wireless mobile communications device such as a smartphone or tablet computer device to control the system.

Preferred embodiments hereof have applications for dermatologists, non-specialists such as primary care physicians and nurse practitioners, and patients able to perform self-measurement. Users of the device can objectively and quantitatively map the contours of a suspect lesion or other skin structure that were previously observed only through simple visual observation and palpation. Stiffness measurements provide a quantifiable metric and a way to determine subcutaneous topology and can be combined with a standard automated image analysis of the lesion to either diagnose or track the evolution of a lesion over time. In accordance with various embodiments, the device can form a map that delineates the margins of a region of interest such as a cancerous lesion that may be shown on a display or stored in a memory. In some embodiments, the devices and methods disclosed herein can provide a surgeon with an augmented view of the surgical landscape to enable real-time, in-situ identification of margins and to reduce revisions during excision.

The devices and methods disclosed herein apply a force or displacement to the tissue and measure tissue deformation or force, respectively, to create a full-field normalized stiffness map that can be used to quantify the stiffness of a cancerous lesion and the healthy tissue surrounding it. A difference in tissue stiffness indicates a higher probability that the lesion is cancerous.

A schematic embodiment of a tissue measurement device according to the present invention is shown in FIG. 1A. The tissue measurement device 5 can include a projector 10 that can include a light source such as an LED, a mask and a lens or lens system, pump 18 or other tissue deflection device as described herein, and a ring emitter 10 such as a ring coupled to the LED, an annular fiber optic array or other source that can uniformly distribute light across the field of view. The projector 10, vacuum pump 18, and ring emitter 10 can be controlled by an interface circuit module 40 that interfaces with a computer 30. The computer 30 may also control a camera 16. The interface module 40 can receive triggering or other information from a user interface 13 such as a button, touchscreen, keyboard or other data entry and control device or from a pressure sensor 12.

In some embodiments, the ring emitter 10, vacuum pump 18, and pressure sensor 12 can communicate with the computer 30 through the interface module 40. In a preferred embodiment, the standard of communication can be Treehopper, a Universal Serial Bus (USB)-based open-source platform for connecting computers, smartphones, and tablets to electronics for signal acquisition, control, and interfacing. However, any suitable communication standard can also be used to facilitate communication among elements of the tissue measurement system 5 including wired and wireless modalities. Computer or data processor 30 can be connected to external data processing and data storage devices via wireless and/or wired networks utilizing secure systems or public access systems such as the internet.

In some embodiments, the interface module 40 includes a primary integrated circuit. In a preferred embodiment, the primary integrated circuit is a PIC16F1459 microcontroller. The primary integrated circuit of the interface module 40 can communicate with the computer 30 using, for example, USB to control the vacuum pump 18, projector 10, or ring emitter 10 or to receive data from the user interface 13 or the pressure sensor 12. In further embodiments, the control system can be connected to a plurality of light sources, light detectors and tissue deflection devices as described herein.

Figure 1B:
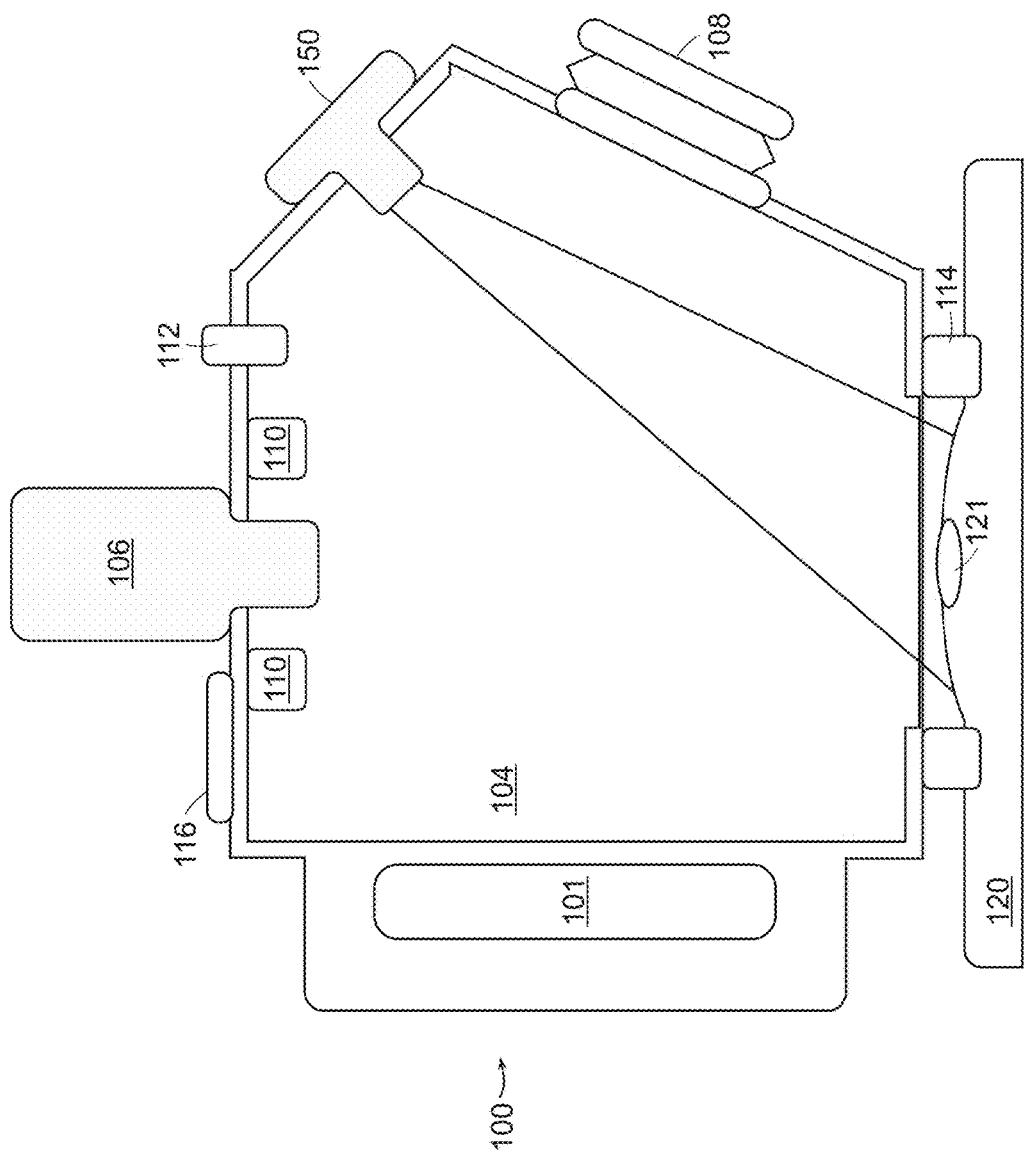
FIG. 1B shows a cross-sectional side view of a tissue stiffness measurement device according to preferred embodiments.

Turning to FIG. 1B, an embodiment of a tissue measurement device of the present invention is shown. The device 100 includes a chamber 104 that can be placed on a patient's skin 120 to assess properties of the skin tissue including stiffness, morphology, and vascularity. A light pattern optical system 150 can project light from a light source into a light pattern on the patient's skin 120 that is imaged by an imaging device 106. The device includes a tissue displacement element in the form of a vacuum system. To measure dynamic properties of the skin 120, a seal 114 placed against the skin 120 can allow a vacuum to be drawn within the chamber 104 using a vacuum pump 108. The level of vacuum inside the chamber 104 may be measured using a pressure sensor 112. A ring emitter 110 may also be provided to uniformly illuminate the skin 120 for visible light image acquisition by the imaging device 106. The electronic and mechanical controls may be implemented and monitored using circuitry formed on a printed circuit board (PCB) 116.

A chamber 104 can be made of any material that fits application specific requirements including, for example but not limited to, poly-methyl methacrylate (e.g., Plexiglas®, Lucite®, or Perspex®), plastics, metals, various glasses and glass compositions, or any combinations thereof. In some embodiments, the walls of the chamber may be opaque or may be coated or covered with an opaque substance to block external light from entering the chamber. To improve usability, the chamber 100 may be equipped with one or more handles 101.

A force or displacement is applied to the tissue to deform it for measurement and calculation of stiffness. In accordance with various embodiments, the applied force can be static or dynamic, and the direction of the force can be solely normal, radial, or torsional to the tissue or may be a combination of more than one directionality applied simultaneously or sequentially. An exemplary radial force can be similar to stretching or pinching while an exemplary torsional force can include twisting. In some embodiments, applied static forces can include direct applied force, indirect applied force such as by a ring placed surrounding the lesion, pneumatics including positive or negative (vacuum) pressure, and any other suitable static force that meets application-specific requirements. Applied static forces may be converted to dynamic forces by imparting oscillations to the above-described static force methods. In addition, dynamic forces may also be applied using acoustic waves from transducers, speakers or a vibration motor. In accordance with various embodiments, the application of forces can be automated using an electromechanical system operating in response to stored control system parameters, or may be manually applied using a mechanical device, such as a flexure-based kinematic linkage.

In the embodiment depicted in FIG. 1B, a vacuum pump 108 acts as a tissue displacement element by applying a light vacuum force (from 0 up to 100 mbar) to the interior of the chamber 104. The vacuum values given are merely illustrative and do not limit the vacuum that can be applied in an exemplary chamber 104. The chamber 104 can be in contact with skin tissue 120 via a custom seal 114. A pressure sensor 112 can be used to monitor the level of vacuum within the chamber 104. In some embodiments, multiple levels of vacuum may be applied sequentially in order to apply different levels of force to the skin tissue 120. Due to the variable contours and viscoelastic properties of skin, applying a known force can be inherently difficult. One advantage of applying a vacuum force along with a custom-designed silicone seal is that the use of negative pressure to pre-load the device against the tissue helps to hold the device rigidly against the skin. In some embodiments, the chamber 104 may hold the negative pressure until the skin tissue 120 reaches a steady state in order to negate viscoelastic effects. The seal 114 and adjacent opening in the chamber 104 may be advantageously sized to fit most or all lesions 121 that may be found on a patient's skin 120 without compromising the ability to seal against a vacuum. For example, the diameter of the custom seal may be between 2 and 12 cm. In a preferred embodiment, the diameter of the custom seal may be 6 cm. For smaller form factor devices, seals with diameters in the 2-4 cm range can be used. In accordance with various embodiments, the vacuum pump 108 may include a syringe or ball pump similar to that on a blood pressure cuff or may include a physical pump or in-house vacuum that can be stepped down and controlled using a pressure regulator. The pressure sensor 112 can be a transducer that is in communication with other components on the custom PCB 116 such that pressure measurements may be recorded and associated with structured illumination or visible light images of the skin 120.

The structured light reconstruction system (i.e., a light pattern optical system 150 and one or more imaging devices 106) and the force application system (in this embodiment, a vacuum pump 108 and pressure sensor 112) are combined along with a custom printed circuit board (PCB) with driver circuitry 116 and a ring emitter 110. The ring emitter 110 is used to evenly illuminate the tissue for visible light images that can be associated with the structured light images and may be utilized for standard image analysis. The PCB 114 includes electronic components to that connect the device 100 to a smartphone, tablet or computer for data I/O. Software can be used to control the lighting, imaging device, and applied force. In some embodiments, the ring emitter 110 or an additional source of light can be used to provide multi-spectral (ultraviolet (UV) or infrared (IR)) light to the tissue. The imaging device(s) may be adapted to receive UV light through, for example although not limited to, choice of light filters. The UV map of the skin can be used to trace vasculature as blood vessels have a much different UV absorption characteristic than surrounding skin.

In some embodiments, it may be advantageous to track the position of the device 100 relative to the skin 120 of a patient. Skin position can be measured and tracked through an optical flow methodology. Optical flow algorithms can begin from a known reference point, e.g. a ring finger tip, and then use camera lens calibration information with optical flow to determine a position on the body relative to the initial reference point. Optical flow enables an estimation of 3D motion based on the motion gradients of features in a sequence of images. Optical flow methodology techniques may be implemented using, for example but not limited to, an optical computer mouse sensor. Optical mice can include a CCD camera and a light source such as a light emitting diode or diode laser. The mouse hardware is interfaced to a computing device through, for example, a USB connection. A mouse filter driver can then enable the extraction of positional data on the skin.

Figure 2:
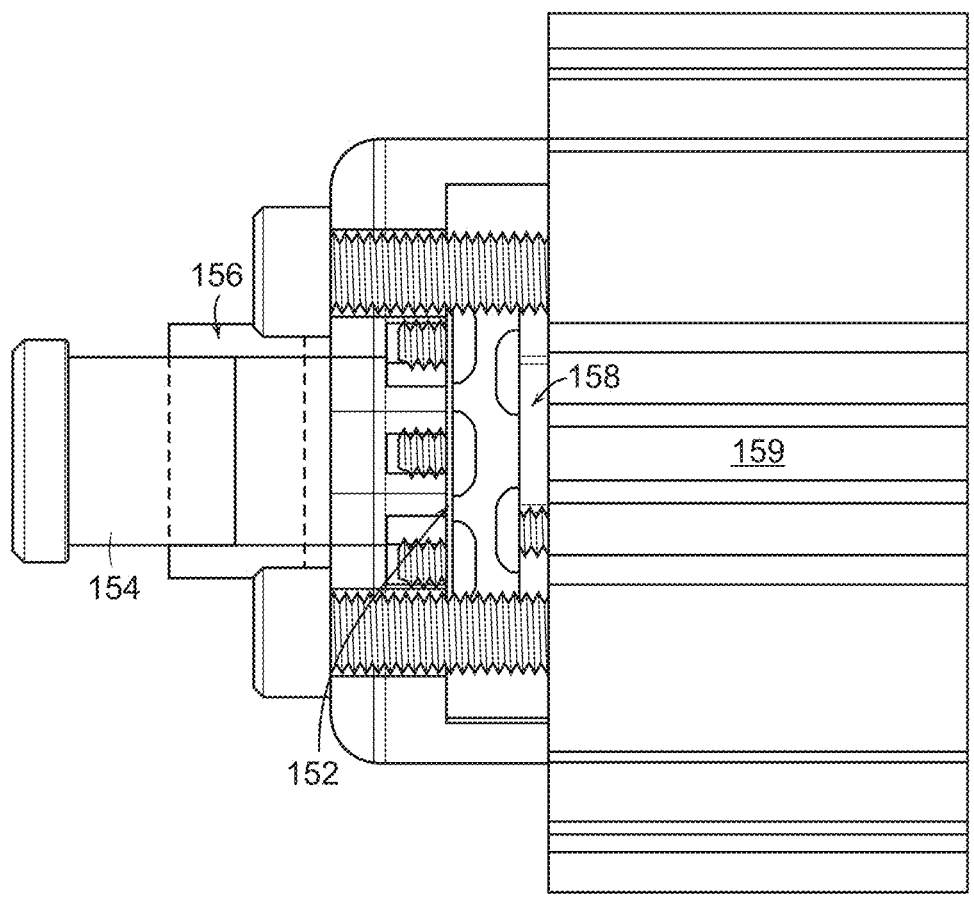
FIG. 2 shows a side cross-sectional view of a light pattern optical system according to preferred embodiments.

With respect to FIG. 2, a larger view is shown of a light pattern optical system according to some embodiments of the present invention. The light pattern optical system 150 can include an LED light source 158 and a projective optic 154 such as a lens. The projective optic 154 may be adapted to the projector using an adapter 156. A mask 152 or other pattern-producing element may be placed between the LED light source 158 and the projective optic 154. In various embodiments, the mask 152 may be a gobo or a digital light projection device such as a DMD/DLP array. The mask 152 can produce light output patterns containing dots, blobs, spaced or hatched lines, or any other suitable pattern shape. An active or passive heat sink 159 can be used to dissipate excess heat generated by the LED light source 158.

The combination of a projective optic 154, a mask 152 producing, for example, a fixed dot pattern, and an LED illumination source 158 creates a structured light pattern that can be projected onto a tissue where it may then be captured by an imaging device 106. Standard camera calibration techniques can identify the projective matrix that relates points in space to points in the imaging devices and projector's respective coordinate frames of reference. Such techniques can also identify the transformation matrix that relates the position and orientation of these two frames of reference. During normal operation, the imaging device 106 can capture still images of the pattern projected onto the tissue 120. In the images, a dot-locating algorithm finds the individual dots in the scene and relates them to the known geometry of the projected dot pattern. A reconstruction algorithm can then use the fixed dot pattern and the observed dot pattern in the imaging device's image to construct a representation in a 3-D space. Because the algorithm knows which of the imaging device dot vectors corresponds with each of the projector's dot vectors the real-world position of each projected dot can be determined using triangulation by analyzing where the vectors intersect in space.

As the structured light pattern is projected onto a surface, the pattern deforms according to the shape of that surface. These deformations can be converted directly into 3-D coordinates that can then be used to create a 3-D reconstruction of the tissue. In various embodiments, the structured light pattern is repeatedly imaged on the tissue as the tissue is deformed to accurately measure tissue displacement.

In some embodiments, the light pattern optical system 150 may include a laser source and a diffractive optical element. The diffractive optical element produces a series of dots, lines, or other patterned light features in the far-field corresponding to the location of the surface of the skin tissue 120. The pattern may be substantially unchanging across the diffracted output or the grating can be chirped or modified to adjust pattern features such as a spatially varying period in one or more dimensions.

Figure 3:
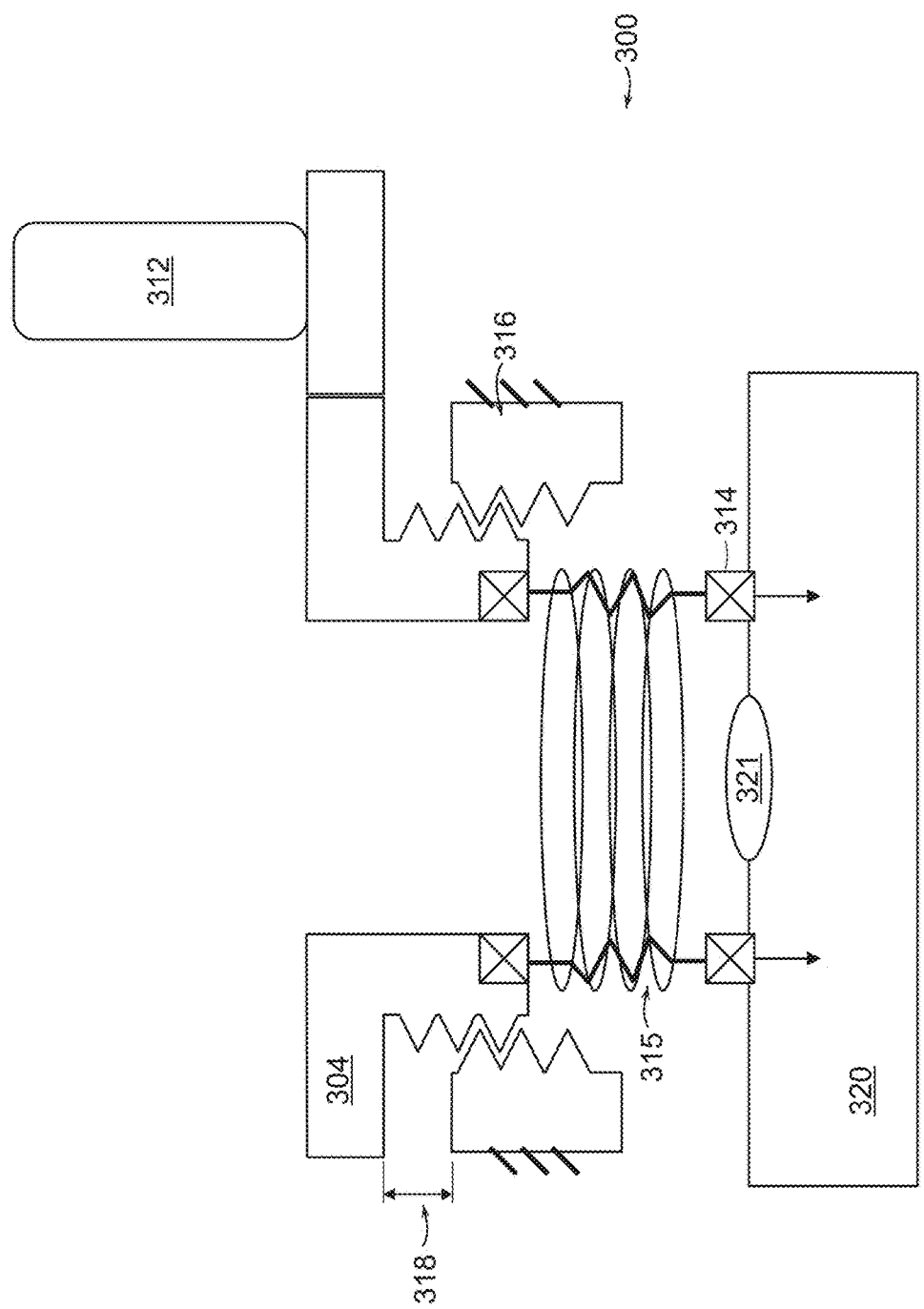
FIG. 3 depicts an embodiment of a flexure-based kinematic linkage force applicator that may be used with tissue stiffness measurement devices according to preferred embodiments.

A flexure-based kinematic linkage force applicator to apply force to a tissue according to various embodiments is depicted in FIG. 3. In some embodiments, a device 300 may be placed on the skin 320 over a suspicious lesion 321. The skin-contacting portion of the chamber 304 includes a spring 315, a threaded or ratcheted portion 316, and a gap 318. In some embodiments, a servo motor 312 may be used to drive the threaded or ratcheted portion 316 in such a way as to reduce the gap 318. A reduction in the gap 318 forces the spring 315 to compress and to apply force to the surface of the skin 320. Applying the force in this way allows for controllable, quantifiable, and repeatable force application based solely on the size of the gap 318 and the spring constant of the spring 315. In some embodiments, the flexure-based kinematic linker can include force and distance transducers and/or a linear encoder. The force or displacement applied to a tissue can be measured in a variety of ways including, but not limited to, capacitive sensors, Hall effect sensors, LVDTs, and photosensors. In embodiments with a photosensor, the photosensor can be positioned as to be gradually occluded by a part of the force applicator as the flexure compresses or decompresses to apply a force or displacement. The reduction in output voltage from the photosensor is directly proportional to the distance moved by the force applicator. In some embodiments, the force applied to the tissue may be insufficient to create a visible morphological change in the tissue surface. For example, tissue stiffness may be measured by measuring the force necessary to just begin to deform the morphology of the tissue. This transition force may then be recorded and correlated to similar measurements of the same site over time or of similar tissue sites in other patients.

Three-dimensional reconstruction may also be done using a digital light processing (DLP) projector to create structured light. Static structured light compares favorably to a DLP projector in some applications because its low cost and power consumption (5 W vs. 250+W) enable it to be easily paired with a smartphone (which can provide a camera, CPU, and internet connection).

Figure 4:
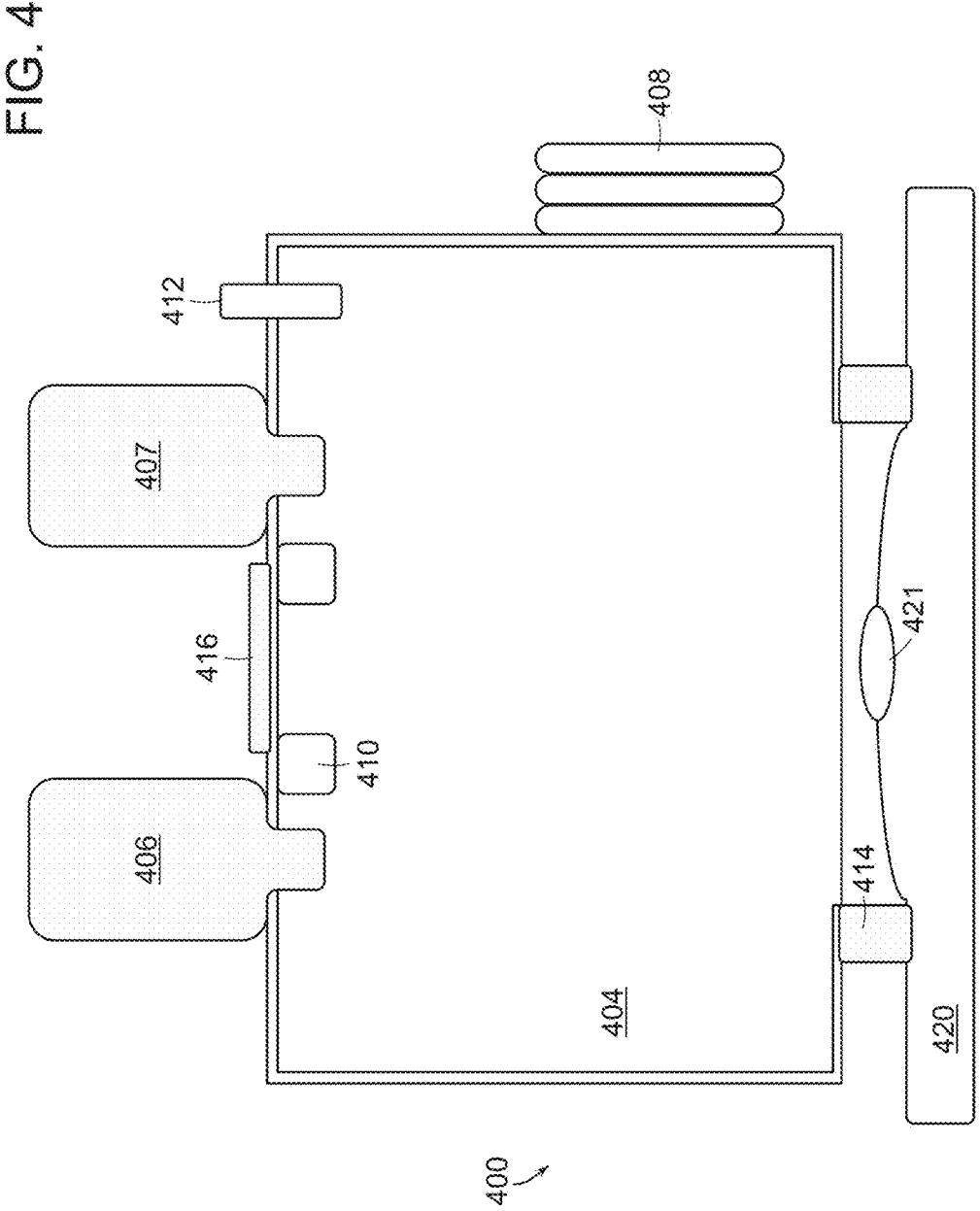
FIG. 4 depicts a tissue stiffness measurement device containing two imaging devices according to preferred embodiments.

Turning now to FIG. 4, a tissue stiffness measurement device is shown that utilizes stereo reconstruction. The device 400 may include two or more imaging devices 406, 407 that each view a skin tissue 420 containing a suspicious lesion 421 from different positions. In accordance with various embodiments, the device may include a chamber 404, a ring emitter 410, a vacuum pump 408, a pressure sensor 412, a custom PCB 416, and a custom seal 414.

The imaging devices 406, 407 may be arranged in any configuration to view the tissue 420 that meets application-specific requirements. In an exemplary embodiment, the centers of the imaging devices 406, 407 can be offset by equal distances from the center of the custom seal 414. The imaging devices 406, 407 may be placed such that their sensors are coplanar or they may be placed such that the relative planar orientation of their sensors is skewed.

In stereoscopic imaging, an algorithm is used to compare pixels in images from each of the imaging devices. When the algorithm has identified the same feature in each of the pictures, the pixel location of the feature can be compared between the two images. Combined with knowledge of the geometrical features of the device including distance between the centers of the imaging devices, depth information can be derived for each point within the field of view. In some applications, structured light (an active reconstruction method) can be advantageous over stereo reconstruction (a passive method) because it can be extremely easy to implement and doesn't depend on the scene.

Figure 5:
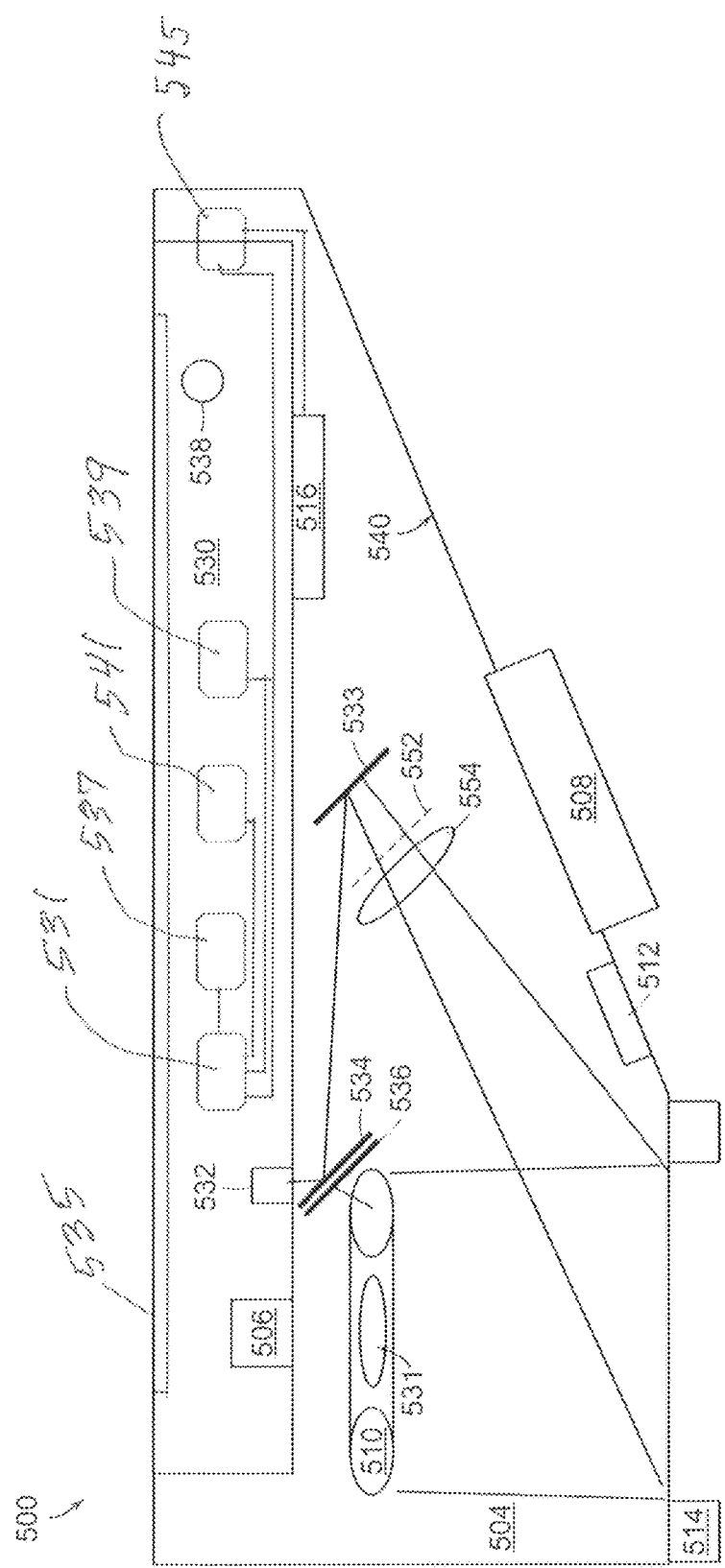
FIG. 5 depicts an embodiment of the present invention that includes a handheld wireless mobile communications device such as a smartphone.

FIG. 5 illustrates an embodiment of a tissue stiffness measurement device that includes a handheld wireless mobile communications device such as a smartphone. A tissue measurement device 500 can use a smartphone 530 to provide an interface for the user as well as processing 531 memory and data storage 537 capabilities. A camera 506 and an LED 532 attached to the smartphone (or tablet) 530 may also be advantageously used to provide imaging and illumination capabilities. The device 500 may be ergonomically shaped as a handle or grip 540 to improve the ease of gripping by a user. The device 530 can be detachably connected to the measurement unit 540. To improve portability, the tissue displacement component of the device 500 may be a small electric pump or button pump 508 that can be operated manually by the hand of a user. In accordance with some embodiments, a seal 514 can ensure that vacuum is maintained within the chamber 504 of the device 500. Custom driver circuitry 516 can be used to operate the components of the device 500.

The device 500 may contain a ring light 510 to evenly illuminate the tissue for visible light imagery that can then be associated with structured light images and also may be utilized for standard or spectroscopic image analysis. In some embodiments, the ring light 510 may comprise a halo-shaped component that collects and re-emits the light from the LED 532 to uniformly illuminate a tissue surface. The halo-shaped component may include frosted glass or plastic materials. The camera 506 of the smartphone 530 can directly image and display a tissue surface using a display 535. A further embodiment can use additional magnifying optics and polarization filters 531 that are placed between the camera 506 and the tissue surface. Device 530 can be powered by battery 539 and the detachable displacement measurement unit can be powered by the same or a second battery in measurement unit 540. A data port, such as USB connector 945 can also connect the device 530 to the unit 540 components such as control circuitry and/or processor 516.

Light from the LED 532 may be shared between the ring light 510 and the light path to the projector using a half-mirror 534 and a liquid crystal device 536. The liquid crystal 536 can be used in part to determine the distribution of light among the paths. Light from the LED 532 may also reflect from a mirror 533 and pass through a mask 552. In various embodiments, the mask 552 can be a gobo or a DMD/DLP array. A focusing lens 554 can focus the structured light from the mask 552 onto a tissue surface.

In some embodiments, an audio connector 538 of the smartphone 530 may be used to allow components of the device 500 to perform analog communication with the processor 531 and data storage of the smartphone 530. For example, the processor of the smartphone 530 may monitor pressure values inside the device 500 by communicating through an audio connector 538 with a pressure transducer 512. Similarly, output from an audio connector 538 can be used to drive the liquid crystal device 536. In accordance with various embodiments, components of the device 500 may also communicate with the smartphone 530 through a digital I/O port including, but not limited to, a mini- or micro-USB connector 545 or various proprietary digital ports. The device 500 can include a wireless transceiver 541 to facilitate communication between the smartphone 530 and other elements of the device 500 including the liquid crystal device 536 or to facilitate communication between the device 500 and external computers or networks including public networks.

Figure 6:
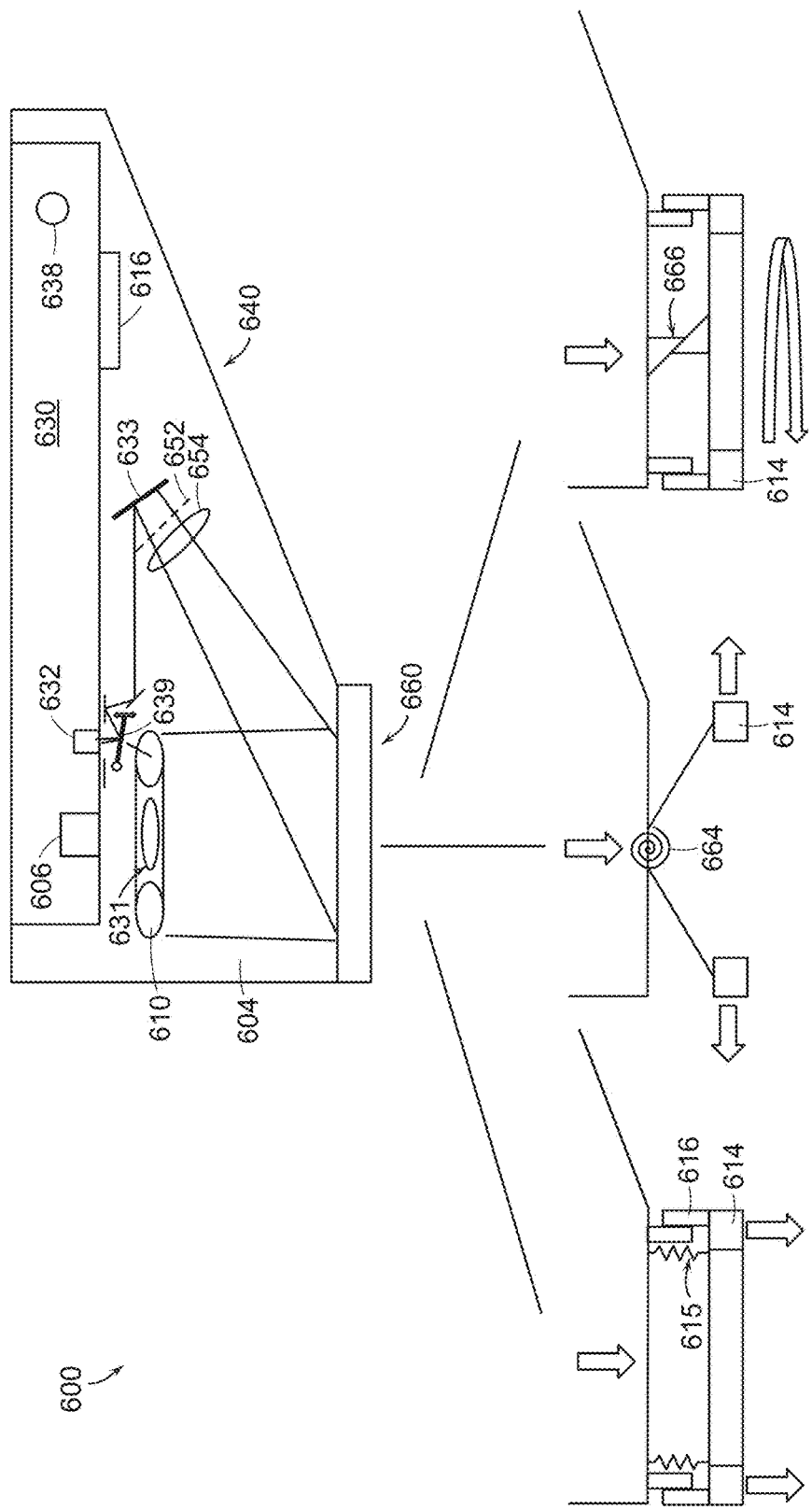
FIG. 6 depicts embodiments of the present invention that include a handheld wireless mobile communications device such as a smartphone and utilize several embodiments of force applicators according to the present invention.

An alternate embodiment of a tissue stiffness measurement device 600 that includes a handheld wireless mobile communications device such as a smartphone 630 is depicted in FIG. 6. The device 600 may include a voice coil driven mirror 639 and a flexure-based kinematic linkage force applicator 660. Components of the device 600 may interface with an audio connector 638 of the smartphone 630 to provide analog communication between elements of the device 600 and the processor and data storage of the smartphone 630. In accordance with various embodiments, components of the device 600 may also communicate with the smartphone 630 through a digital I/O port including, but not limited to, a mini- or micro-USB connector or various proprietary digital ports.

A flexure-based kinematic linkage force applicator 660 of the present invention can provide variable levels of force and tissue displacement in one or more directions. For example, the force applicator 660 may apply a normal force, a radial force, a torsional force, or any other suitable force. Similarly, the resulting tissue displacement can be normal, radial, or torsional to the tissue surface. To apply a normal force, the applicator 660 may include a seal 614, a spring 615, and a threaded or ratcheted portion 616 similar to that described above with reference to FIG. 3. To apply a radial force, the applicator 660 may include a coiled spring 664 that is linked to an expandable seal 614 such that the radius of the seal can be increased or decreased. To apply a torsional force, a block system 666 can be driven by a linear force to produce a twisting force.

In some embodiments, the LED 632 shines light onto a voice coil driven mirror 639 that may be half-mirrored or have other similar beamsplitting properties. For example, output from the audio connector 638 can be used to power motion of the voice coil driven mirror 639. The deflection of the voice coil driven mirror 639 can change the optical path of light from the LED 632 through the mask 652 and focusing lens 654. This path variation can be used to help align the illumination onto a tissue surface.

Figure 7:
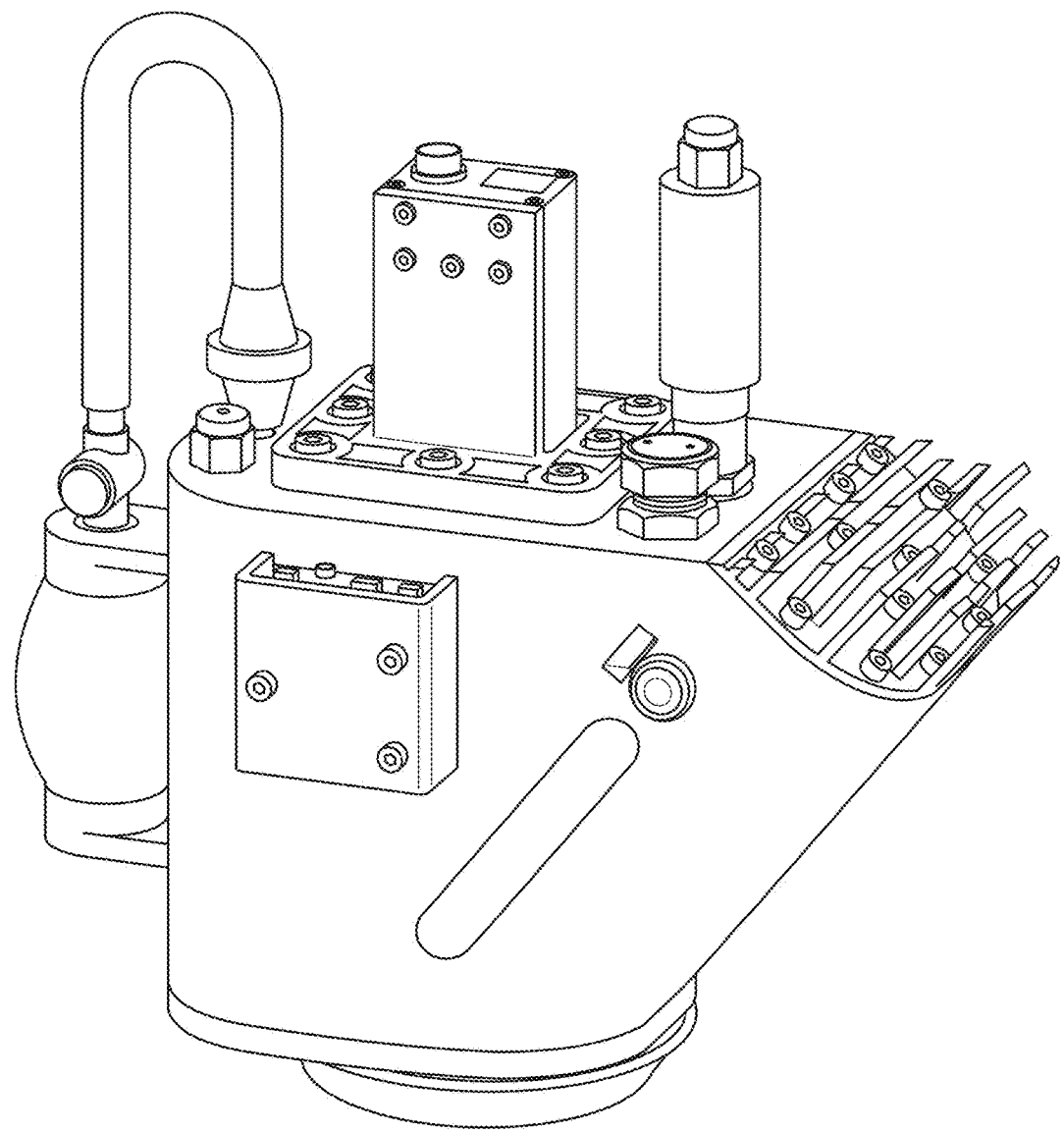
FIG. 7 depicts a perspective view of a portable embodiment according to the present invention.
Figure 8:
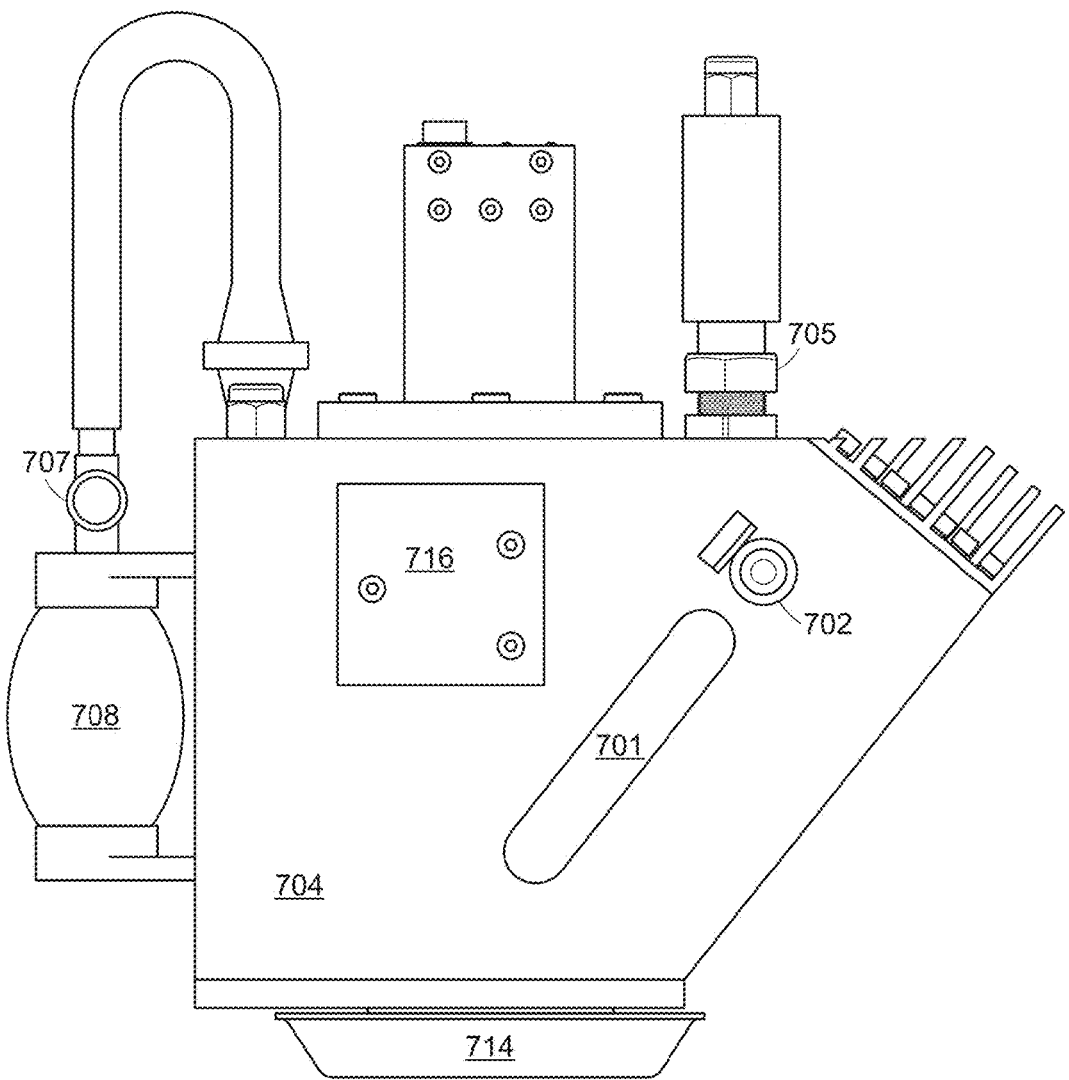
FIG. 8 depicts a side view of the portable embodiment of FIG. 7.
Figure 9:
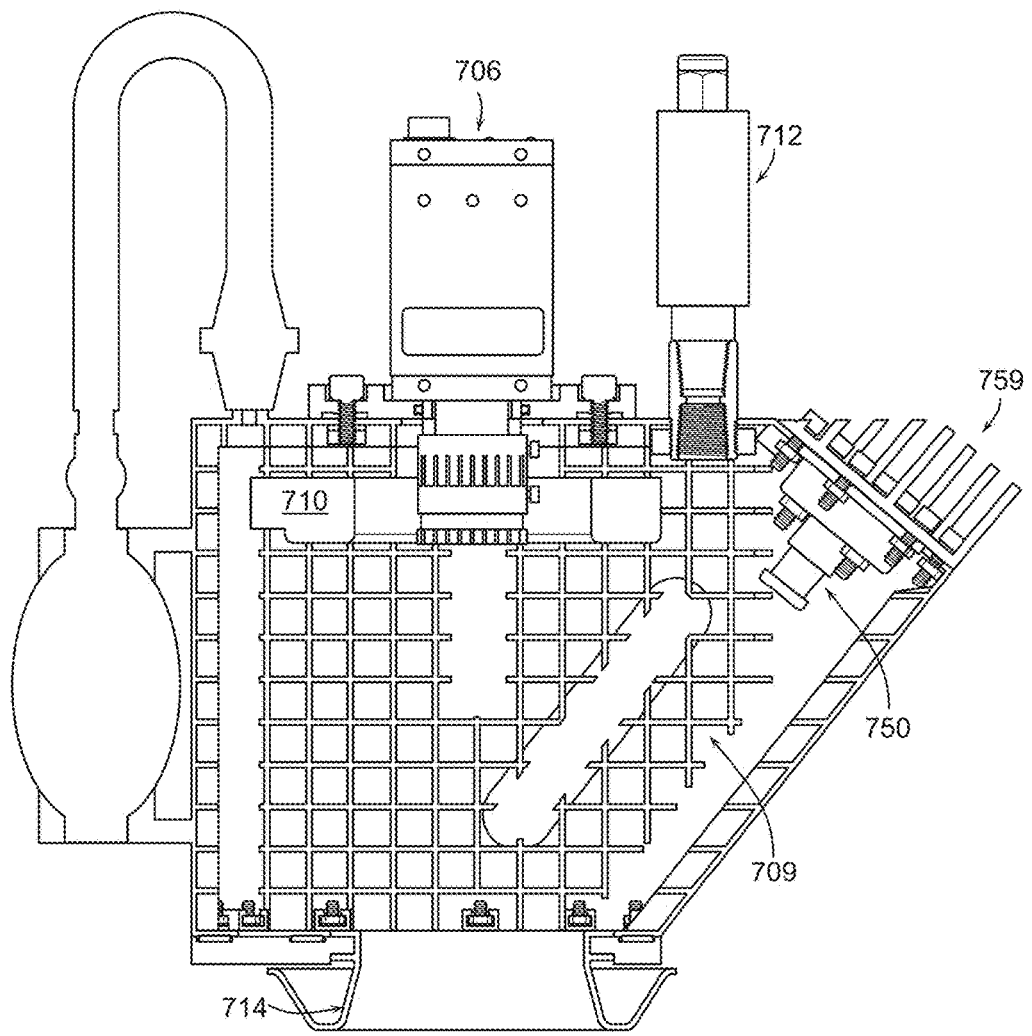
FIG. 9 depicts a cross-sectional view of the portable embodiment of FIG. 7.

An exemplary embodiment of a portable device 700 according to the present invention is shown in several views in FIGS. 7-9. To improve portability, the device 700 may be equipped with a ball pump 708 to produce a vacuum within the chamber 704. In some embodiments, the ball pump 708 can also act as a handle for the device 700. The device 700 may be equipped with a release valve 707 and an operation button 702. The release valve 707 can be used to quickly vent the chamber 704 when the device 700 is to be removed from the patient. The button 702 can start and stop operation of the device 700. The device 700 may also be equipped with a grip handle 701 and cord grips 705 that can provide an airtight port for internal wires to exit the chamber 704 and connect to a custom PCB 716. The chamber 704 can include internal ribs 709 to optimize the enclosure by improving the strength-to-volume ratio of the device 700. Similar to that described above with reference to FIGS. 1-3, the device 700 can include a projector 750, pressure transducer 712, ring light 710, camera 706, and custom seal 714.

Figure 10:
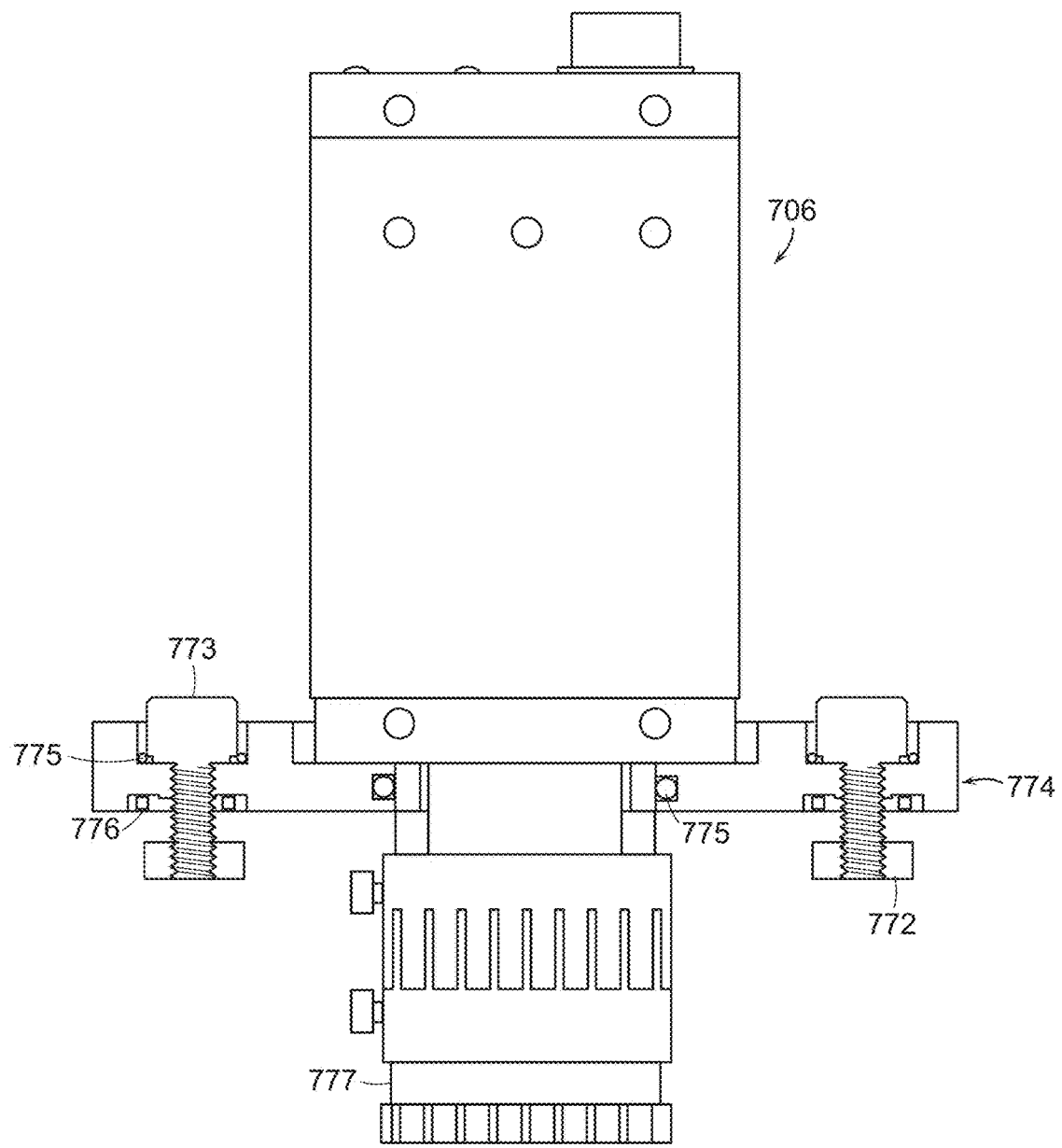
FIG. 10 depicts a cross-sectional view of the camera of the portable embodiment of FIG. 7.

FIG. 10 displays a cross-section of the mounted camera 706 of the portable device 700 shown in FIGS. 7-9. The camera 706 can include a lens or lens system 777. An adapter 774 can be used to mount the camera in place in the device 700. An o-ring 775 can prevent pressure leaks around the camera while gaskets 776 between the nuts 772 and screws 773 can prevent pressure leaks through the screw holes.

Figure 11:
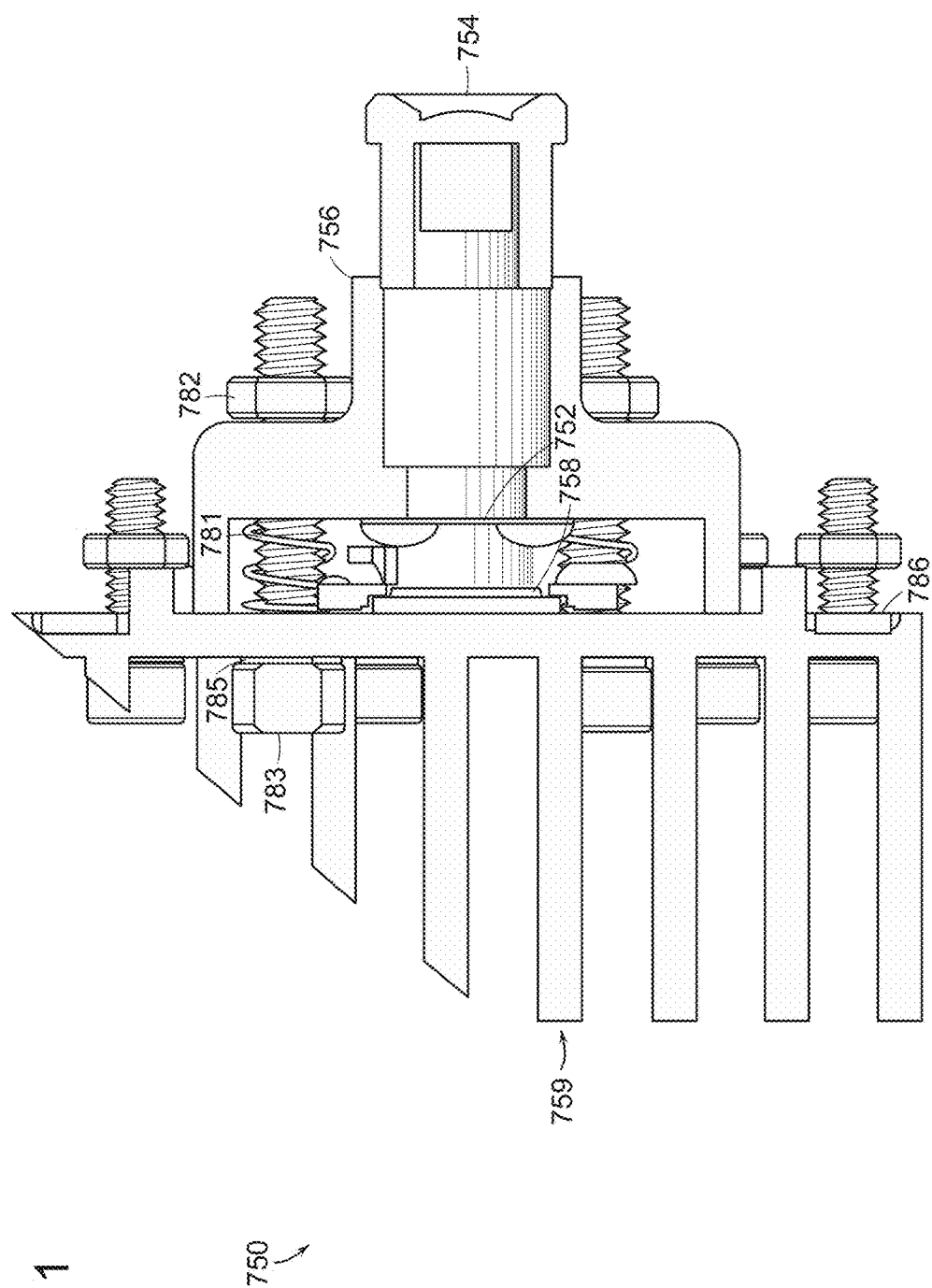
FIG. 11 depicts a cross-sectional view of the projector of the portable embodiment of FIG. 7

FIG. 11 displays a cross-section of the projector mount of the portable device 700 shown in FIGS. 7-9. The projector 750 can include a heat sink 759, LED 758, gobo 752, lens 754, and lens adapter 756. The projector 750 is mounted to the chamber 704 of the device using gaskets 786 between the screws 783 and nuts 782 to prevent pressure leaks. A second set of screws 783 can attach the adapter 756 to the heat sink 759 with a spring 781. An o-ring 785 may also be used near the heads of these screws 783 to help prevent leaks. The springs 781 on these screws 783 can provide a slight angular adjustment of the direction of the lens 754 after it is mounted to the chamber 704.

Figure 12A:
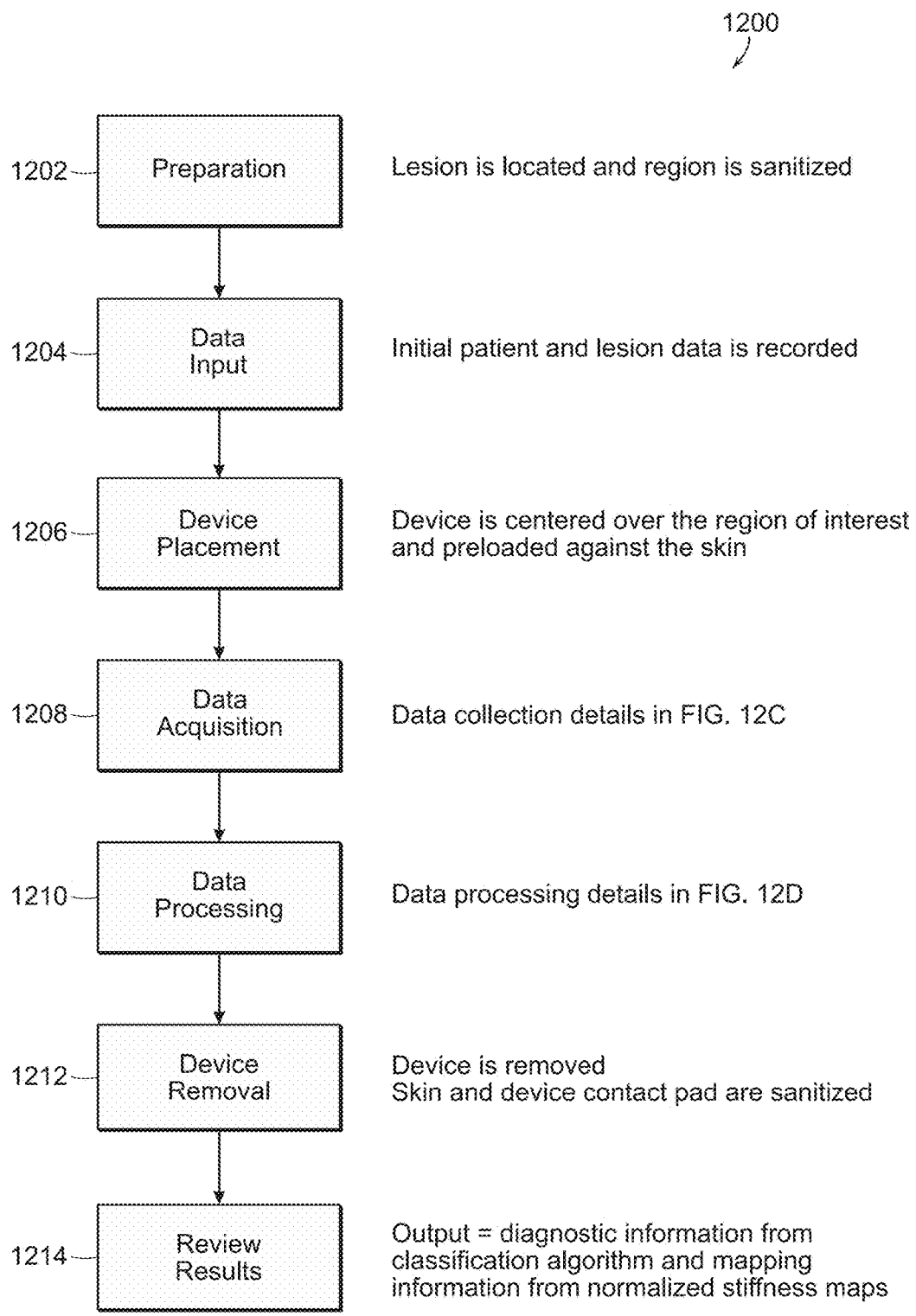
FIG. 12A depicts an example flowchart including a tissue stiffness measurement procedure in accordance with various embodiments of the present invention.

In FIG. 12A, an example flowchart 1200 is depicted including a tissue stiffness measurement procedure in accordance with various embodiments of the present invention. The flowchart 1200 includes the high-level physical steps that can occur during a tissue stiffness diagnostic measurement.

In the preparation step 1202, a suspect lesion can be identified, and the region to be measured can be sanitized. In the data input step 1204, initial patient demographics and lesion data can be recorded. In some embodiments, the demographic and lesion data can include a timestamp; patient information such as patient identification code, age, sex, ethnicity, or skin tone; or lesion information such as location or type. In some embodiments, the patient information can be associated with an anonymous patient identification code so that the patient cannot be personally identified.

In the device placement step 1206, the device can be placed against the skin of the patient. In a preferred embodiment, the device can be centered over the region of interest. The device can acquire data in the data acquisition step 1208. In some embodiments, the data acquisition process can be performed twice, once for the lesion and once for assumed healthy tissue on a region of the body symmetric to the location of the lesion. During subsequent analysis, the lesion and no lesion regions can be compared to generate a relative stiffness measurement. A relative measurement can mitigate boundary condition effects that may be caused by the seal. The data acquisition step 1208 will be described in greater detail below with reference to FIGS. 12B and 12C. At any time after the data acquisition step 1208 is complete, the device can be removed from the patient in a device removal step 1212. The patient's skin and a contact pad of the device can be sanitized.

After the data acquisition step 1208, the data can be processed in a data processing step 1210. During the data processing step 1210, acquired data can be analyzed in combination with the demographic data to produce a diagnosis or elasticity mapping of the lesion. The data processing step 1210 is described in greater detail below with reference to FIGS. 12B and 12D. The patient or a clinician can review the results 1214. In a preferred embodiment, results for review can include diagnostic information from the classification algorithm or mapping information using normalized stiffness maps.

Figure 12B:
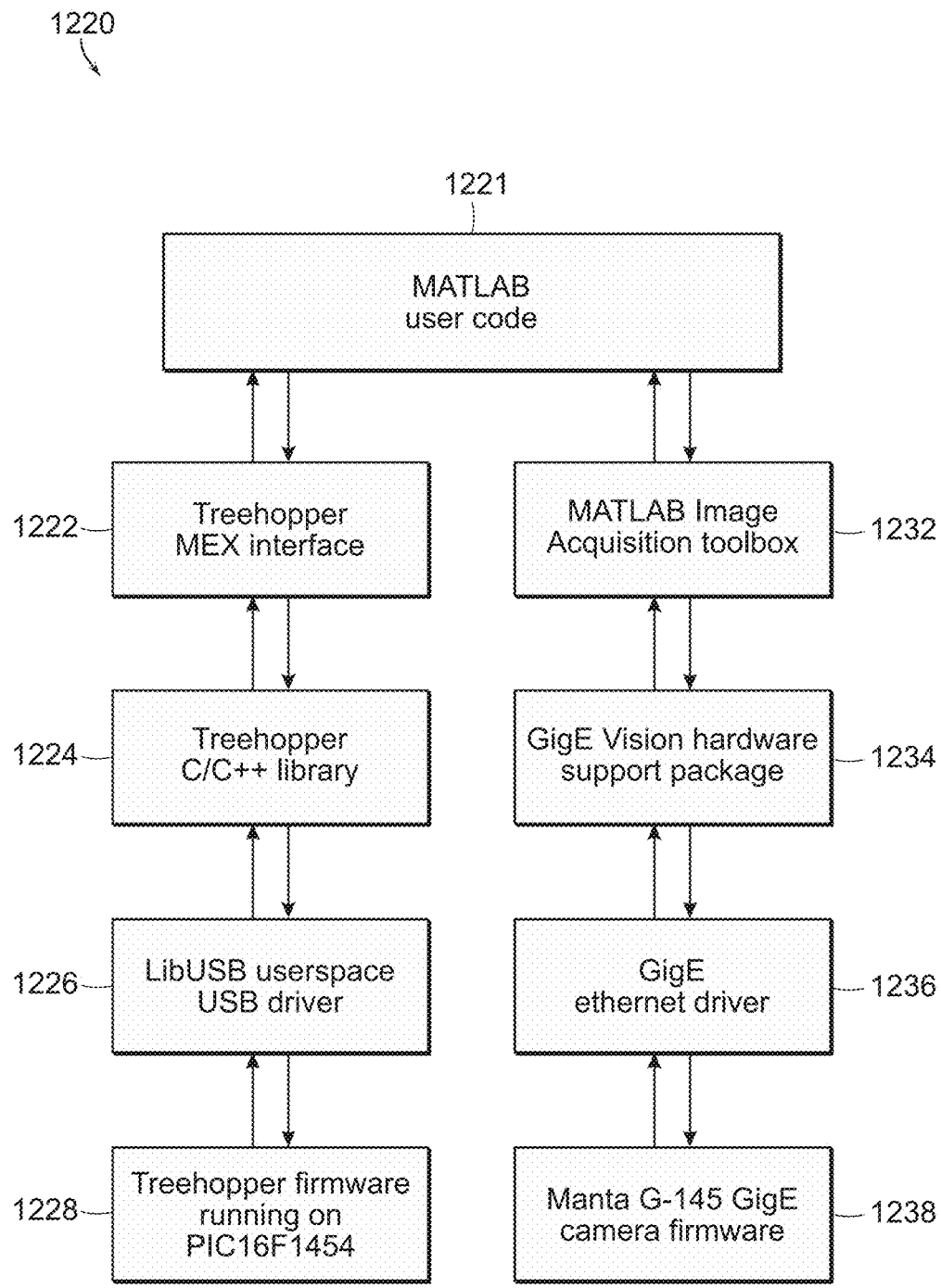
FIG. 12B depicts an example software architecture diagram in accordance with various embodiments of the present invention.

In FIG. 12B, a schematic representation is depicted of a software architecture diagram according to various embodiments of the present invention. The depicted data acquisition and device control function blocks can be implemented in software. In some embodiments, the function blocks can be implemented using MATLAB user code 1221 (e.g., scripts). In some embodiments, the MATLAB user code 1221 can control hardware.

In some embodiments, the MATLAB user code 1221 can interface with a Treehopper MEX interface 1222. In turn, the Treehopper MEX interface 1222 can access or interface with a Treehopper C/C++ library 1224. The Treehopper C/C++ library 1224 can provide an interface to a LibUSB userspace 1226 including a USB driver. The LibUSB userspace 1226 can communicate with the Treehopper firmware running on a primary integrated circuit such as a PIC16F1454 included in the interface module 40 or custom PCB 116, 416, 716.

In some embodiments, the MATLAB user code 1221 can interface with or include elements of the MATLAB Image Acquisition toolbox 1232. The MATLAB Image Acquisition toolbox 1232 can interface with a GigE Vision hardware support package 1234. The GigE Vision hardware support package 1234 can interface with a GigE Ethernet driver 1236 that, in turn, can interface with Manta G-145 GigE camera firmware 1238, for example.

Figure 12C:
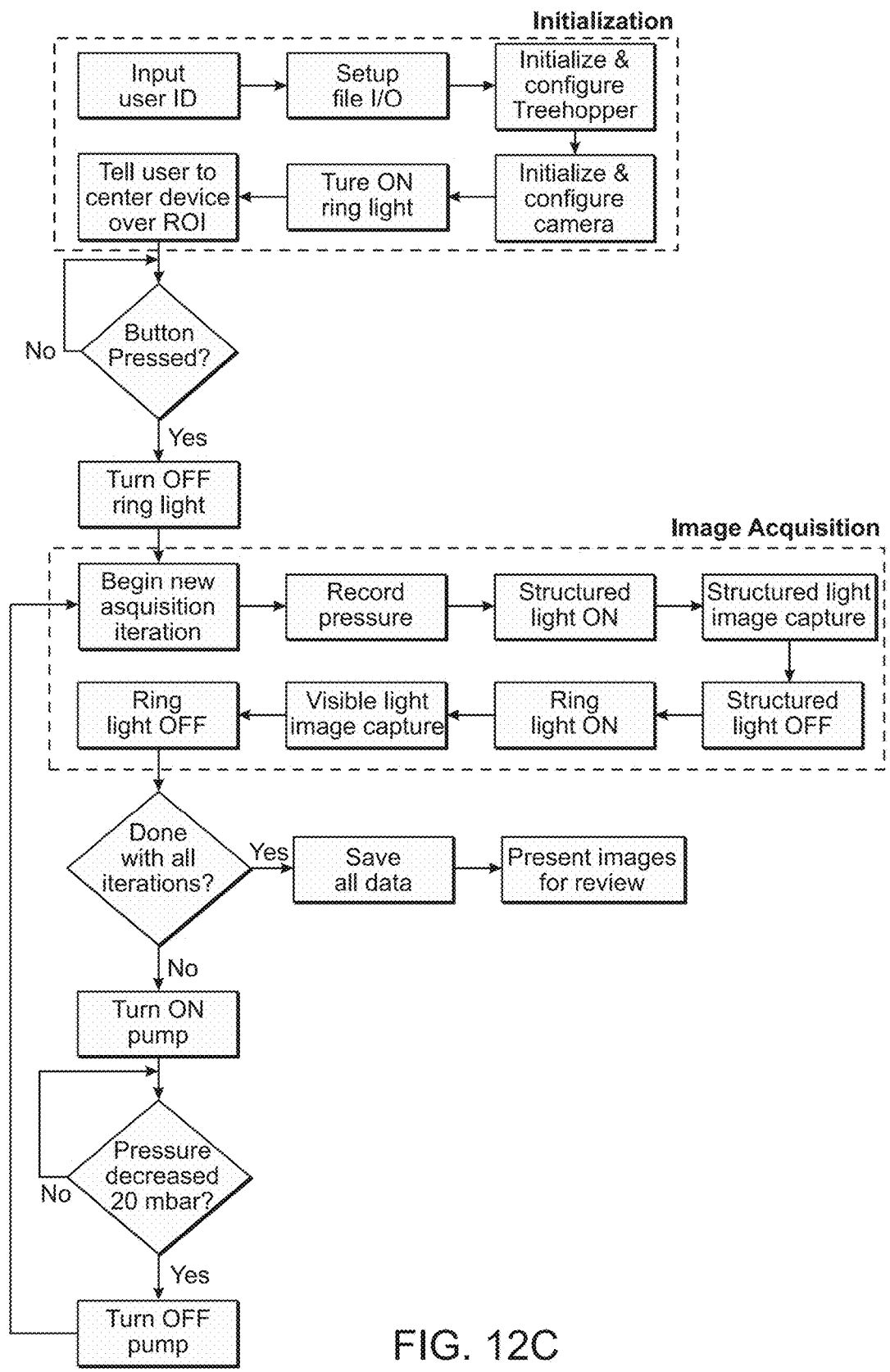
FIG. 12C depicts an example computational flow map for data acquisition according to some embodiments of the present invention.

In FIG. 12C, an example computational flowmap is depicted for data acquisition. In some embodiments, the data acquisition flowmap can be a subroutine of the data acquisition step 1208 of the schematic procedure depicted in FIG. 12A. The data acquisition flowmap can be implemented using a graphical user interface (GUI) in some embodiments. The GUI can enable the user to view the camera view or the present status or stage of the procedure.

An initialization process can be performed during data acquisition. A user ID can be inputted and file input and file output (I/O) can be set up. For example, the directory may be set up where data will be saved. The camera and interface control module (e.g., Treehopper) can be initialized. The ring emitter can be turned on so that the user can see the view from the camera. The GUI can ask the user to center the device over the region of interest and to activate the user interface (e.g., press the button) when ready.

After the initialization process, the script can wait until the button is pressed by the user. Once the button is pressed, the ring light can turn off and an image acquisition sequence can begin.

The image acquisition sequence can include several elements. For each iteration of the image acquisition sequence, the current pressure can be recorded. The projector can be turned on and an image can be captured including structured light. Next, the projector can be turned off and the ring emitter can be turned on. With the ring emitter on, a visible light image can be recorded by the camera. The ring emitter can then be turned off.

At this stage of the image acquisition procedure, the computer, interface module, or custom PCB can determine whether all iterations have been completed. If no more iterations of the image acquisition sequence are needed, the data can be saved and processed and images can be presented for review. If further iterations are required, the flowmap proceeds to turn on the pump.

In some embodiments, the device can be set to capture images for pressures of 0-100 mbar in 20 mbar increments. For each further iteration, the pump can lower the pressure by 20 mbar relative to the previous pressure value. When the pressure has been decreased by 20 mbar relative to the prior value, the pump can be turned off. The computer, custom PCB, or interface module can engage the image acquisition sequence to acquire additional images at the new pressure value. In some embodiments, the sequence can repeat until data is captured for all relevant pressure levels. If the user locates errors in one or more of the images, some or all of the data acquisition process can be repeated. In some embodiments, the data acquisition sequence can be performed on tissue that includes a suspicious lesion and on presumed healthy tissue symmetrically located on the patient with respect to the lesion.

Figure 12D:
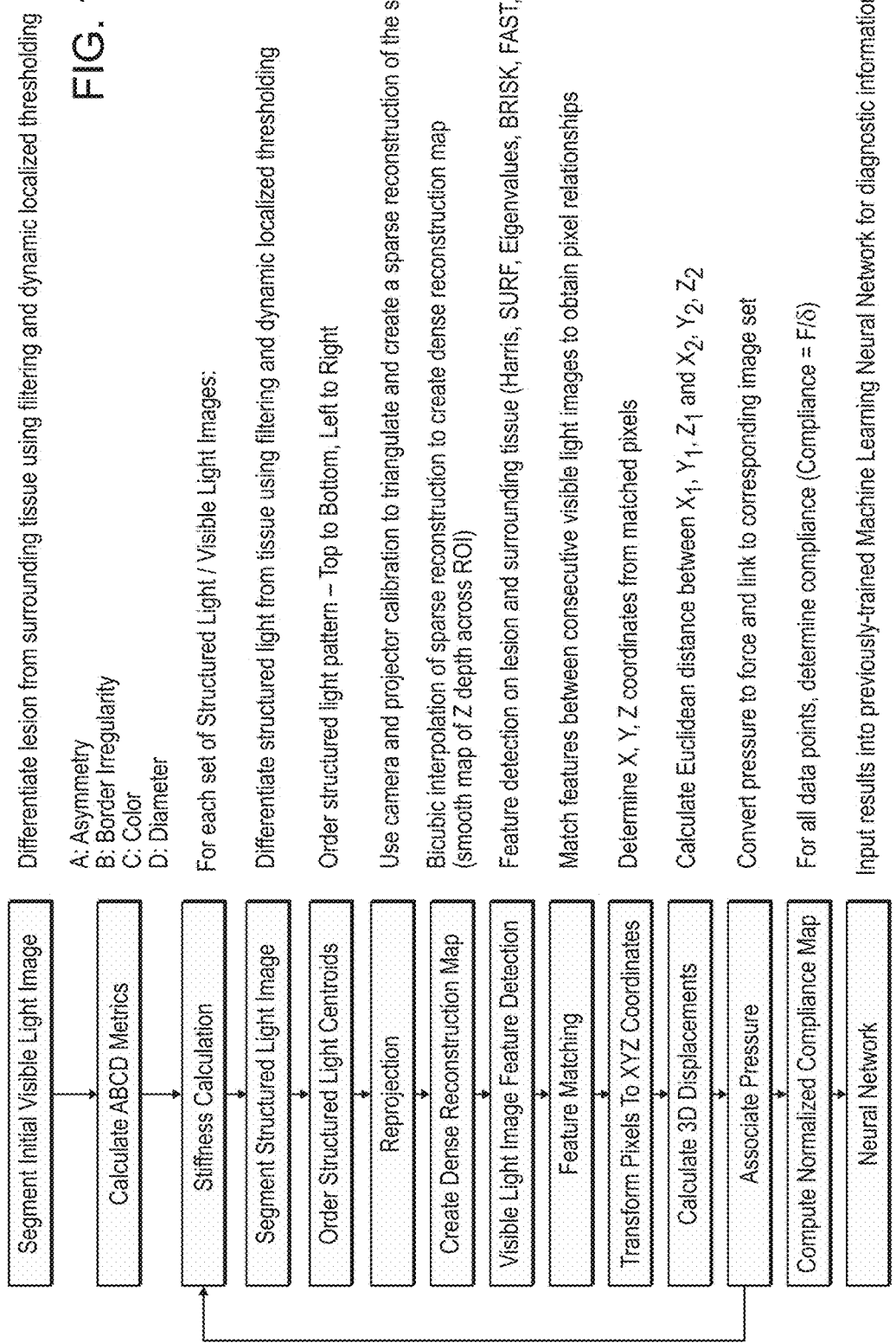
FIG. 12D depicts an example computational flow map for processing acquired image data according to some embodiments of the present invention.

After visible light and raw images are acquired at several applied force values, a data processing algorithm may be used to extract various parameters and metrics from the images. An exemplary flow map of the data processing algorithm is depicted in FIG. 12D according to various embodiments. In this embodiment, the raw images are in the form of structured light images; however, the flow map is fundamentally the same for other types of raw image including stereo reconstruction. The visible light and raw structured light images may be segmented. In the visible light images, the suspicious lesion can be differentiated from surrounding tissue while segmentation of the structured light image differentiates the structured light from the tissue. The segmentation techniques may include filtering and dynamic localized thresholding. Based on the segmented visible light image, measures based on the ABCD metrics (asymmetry, border irregularity, color, and diameter) can be calculated. Based on the segmented structured light image, centroids of the structured light pattern may be ordered. Using the calibration and geometric orientation of the imaging device and projector, a triangulation and sparse reconstruction may be made of the scene. A dense reconstruction map can be generated by applying a bicubic interpolation to the sparse reconstruction. The dense map represents a smooth map of the z-depth across the region of interest.

Various methods may be applied to the visible light image to detect features of the segmented lesion. Methods for feature detection include, but are not limited to, detectors and keypoint descriptors such as Harris, Scale Invariant Feature Transform (SIFT), Speeded-Up Robust Features (SURF), eigenvalues, Binary Robust Independent Elementary Features (BRIEF), Binary Robust Invariant Scalable Keypoints (BRISK), Features from Accelerated Segment Test (FAST), Oriented FAST and Rotated BRIEF (ORB), and Fast Retina Keypoints (FREAK). Once features have been identified in each of the series of visible light images, feature matching can be applied across images to obtain pixel relationships. The matched pixels may be transformed to determine XYZ coordinates. From these coordinates, the 3-D displacements can be calculated as the Euclidean distance between XYZ values in one image and XYZ values in a subsequent or previous image in the series. The process may be repeated until the entire series of images has been processed.

With a complete set of data points in hand, a normalized compliance map can be computed. The compliance is defined as Force (F)/Deflection ($\delta$). In accordance with various embodiments, a machine-learning neural network may be employed to interpret diagnostic criteria including, but not limited to the tissue metrics and stiffness measurements and to provide a diagnosis probability. The neural network may be trained using previously-acquired datasets. The machine-learning neural network may be contained within a database or memory associated with a data processor. In some embodiments, the data processor and memory can be components of a portable computer device such as a smartphone.

Figure 12E:
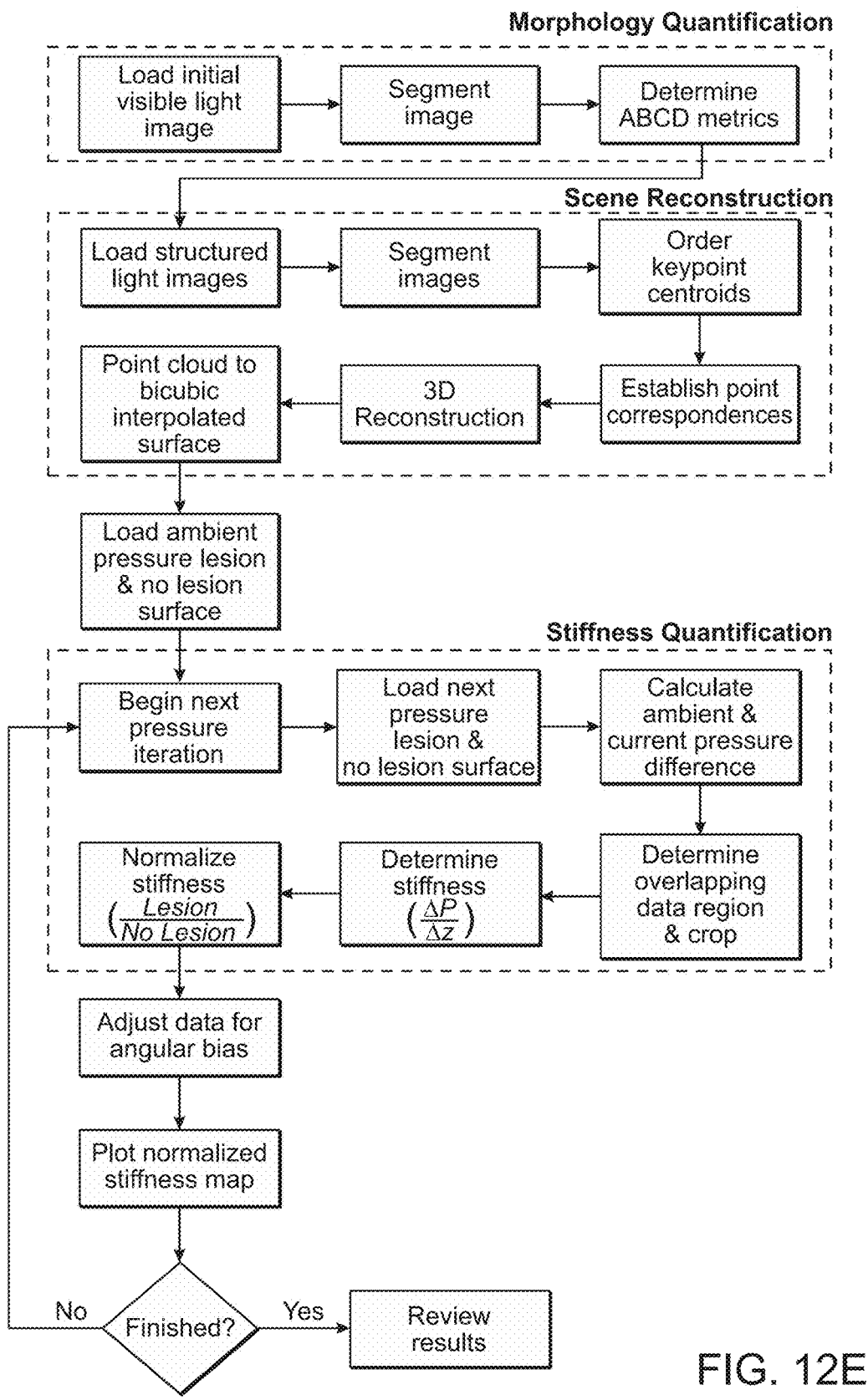
FIG. 12E depicts an example computational flow map for processing acquired image data according to some embodiments of the present invention.

FIG. 12E depicts an example computational flow map for processing acquired image data according to some embodiments of the present invention. The visible light image can be loaded and segmented to differentiate the lesion from surrounding tissue using filtering and dynamic localized thresholding. The ABCDs can be quantified using algorithms as described previously.

Next, the tissue stiffness map can be generated. For each set of structured light images, the projected pattern is differentiated from the background tissue using filtering and dynamic localized thresholding. The keypoints of the light pattern are ordered using algorithms described previously. The camera and projector calibration matrices are then used to triangulate and create sparse reconstructions of the scene. The sparse reconstruction point clouds can then be bicubically interpolated to surfaces. Because bicubic interpolation does not handle discontinuous, limited-domain data well, the surfaces can be carefully cropped to provide accurate data.

Once the structured light images are converted into surfaces, the stiffness quantification process can begin. The ambient pressure surface for the lesion and symmetric healthy region can be loaded and used as references. Surfaces corresponding to images taken at different pressure can then be loaded and the pressure differential can be calculated.

Because surfaces cannot be compared in regions where one surface does not have corresponding data, the stiffness quantification procedure can determine the overlapping data region between all of the images and can crop data outside of this region. At high pressures, and consequently high strains, the tissue can be deformed significantly. As a result, a small part of the high pressure surface may be the only part that overlaps with the original undeflected surface, causing the map to shrink.

The pressure differential for the lesion and non-lesion images may be slightly different, so normalization of the values can be used to allow comparison. In some embodiments, normalized stiffness for individual measurements can be determined by dividing the pressure differential by the calculated surface displacement. Normalized stiffness can be a useful relative metric even though it is not a true Young's modulus value. Tissue elasticity is proportional to the normalized stiffness. In accordance with various embodiments, he normalized stiffness can be further normalized to remove boundary condition effects by comparing the lesion stiffness map to the non-lesion stiffness map.

The elasticity of the lesion can be qualitatively compared with the healthy surrounding tissue through analysis of the normalized stiffness map. ABCDs, stiffness, and demographics can all be input into a classification algorithm for diagnostic information. This information can be used to assist with diagnosis or can be stored and compared to a later measurement to determine if the lesion is evolving. An evolving lesion can be a sign that the lesion is potentially cancerous.

Figure 13:
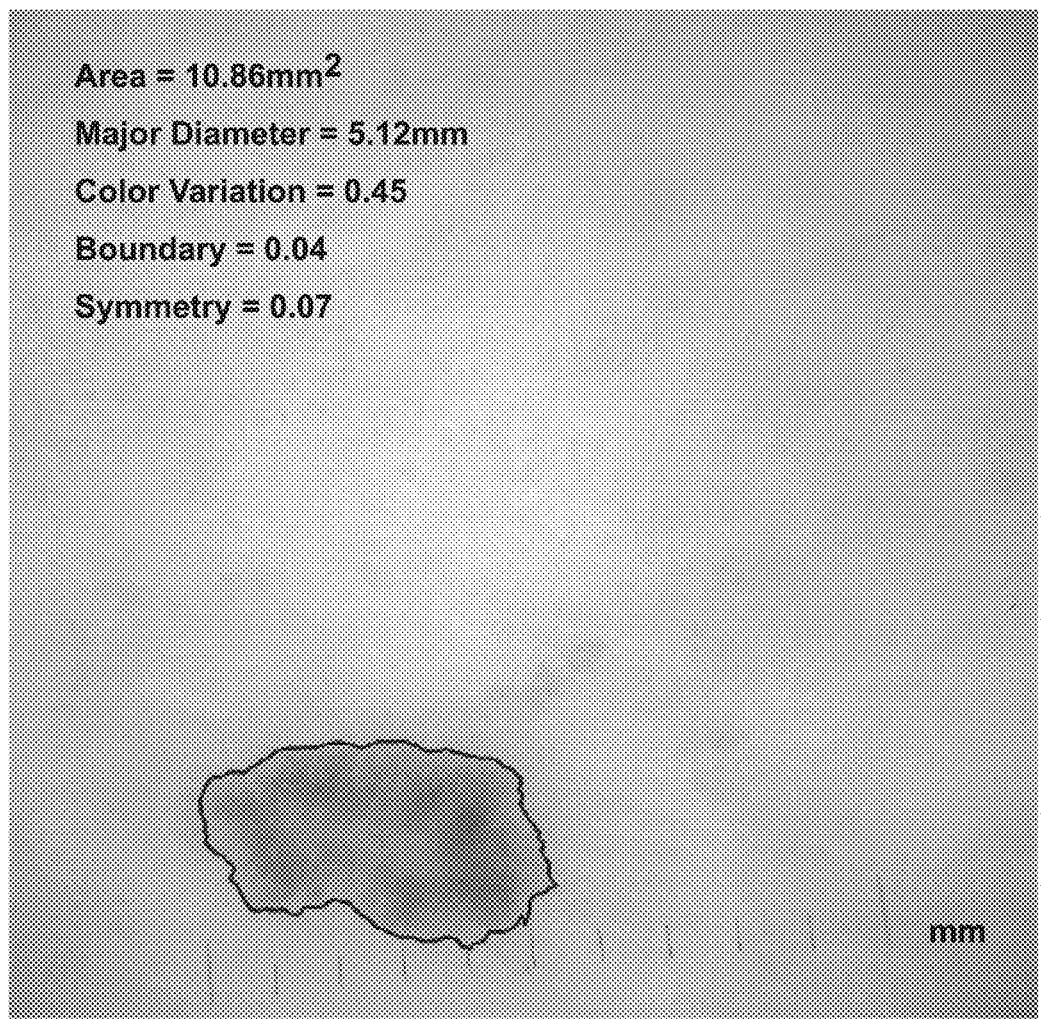
FIG. 13 depicts the quantification of selected metrics of a lesion using a custom algorithm according to preferred embodiments.

FIG. 13 depicts a computational assessment of several metrics of a suspicious lesion as determined by a custom algorithm in accordance with various embodiments. The algorithm can use image processing techniques to identify tissue metrics. The algorithm can determine geometric properties of a lesion including area, symmetry and diameter. In addition, the algorithm can determine color variation and measures of the boundary irregularity. Additional metrics can include measures of vascularization.

Figure 14:
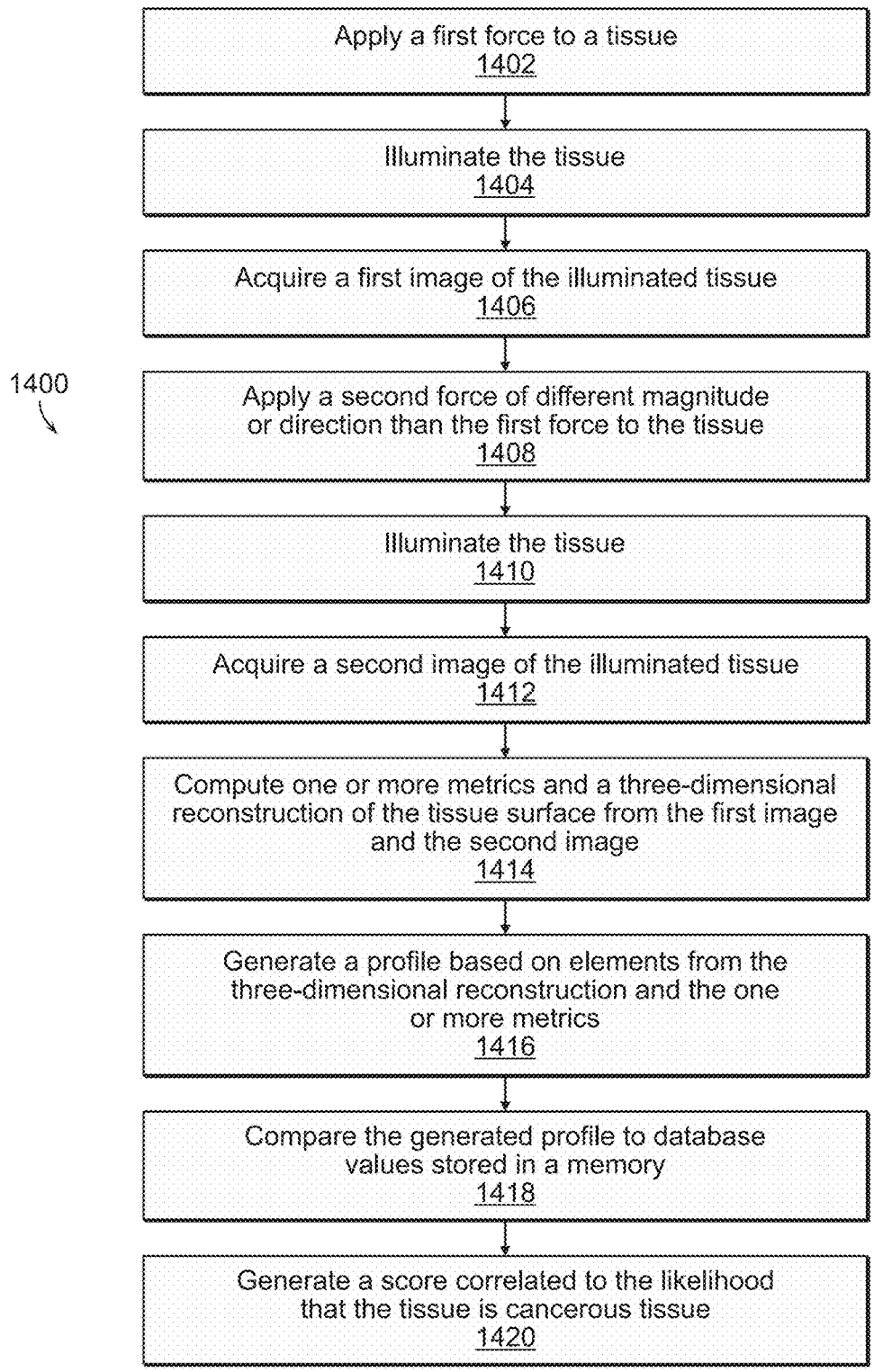
FIG. 14 describes a method of measuring tissue stiffness according to preferred embodiments.

A method of measuring tissue stiffness is demonstrated in FIG. 14. In the method, a force or displacement is applied to the tissue while the tissue is illuminated such that the tissue assumes a first conformation. The illumination may be made using a standard light source, structured illumination, or both. One or more images can be acquired of the illuminated tissue. Then, a force or displacement of different magnitude or direction is applied to the tissue such that the tissue assumes a second conformation, and the tissue is illuminated and imaged again. These steps may be repeated for a number of different forces/displacements to acquire a series of images. One or more metrics may be computed using information from the series of images, and a three-dimensional reconstruction of the tissue surface can also be computed. The computed metrics can include but are not limited to visually assessed indicators or maximum displacement features as mentioned previously. The computed metrics and the three-dimensional reconstruction can then be used to generate a profile that may be compared to database values stored in a memory. In accordance with various embodiments, the values may be compared between measurements of the same lesion over time or may be compared to a database of values obtained from other individuals and/or other lesions, or using a model of such data. In addition, a comparison of the computed metrics or values with reference data such as a previously-trained dataset leads to the generation of a score that is correlated to the likelihood that the tissue is cancerous.

FIG. 15 depicts the repeatability of an exemplary algorithm in terms of maximum, average, and standard deviation of voxel locations and system magnification over repeated image acquisitions.

Figure 16:
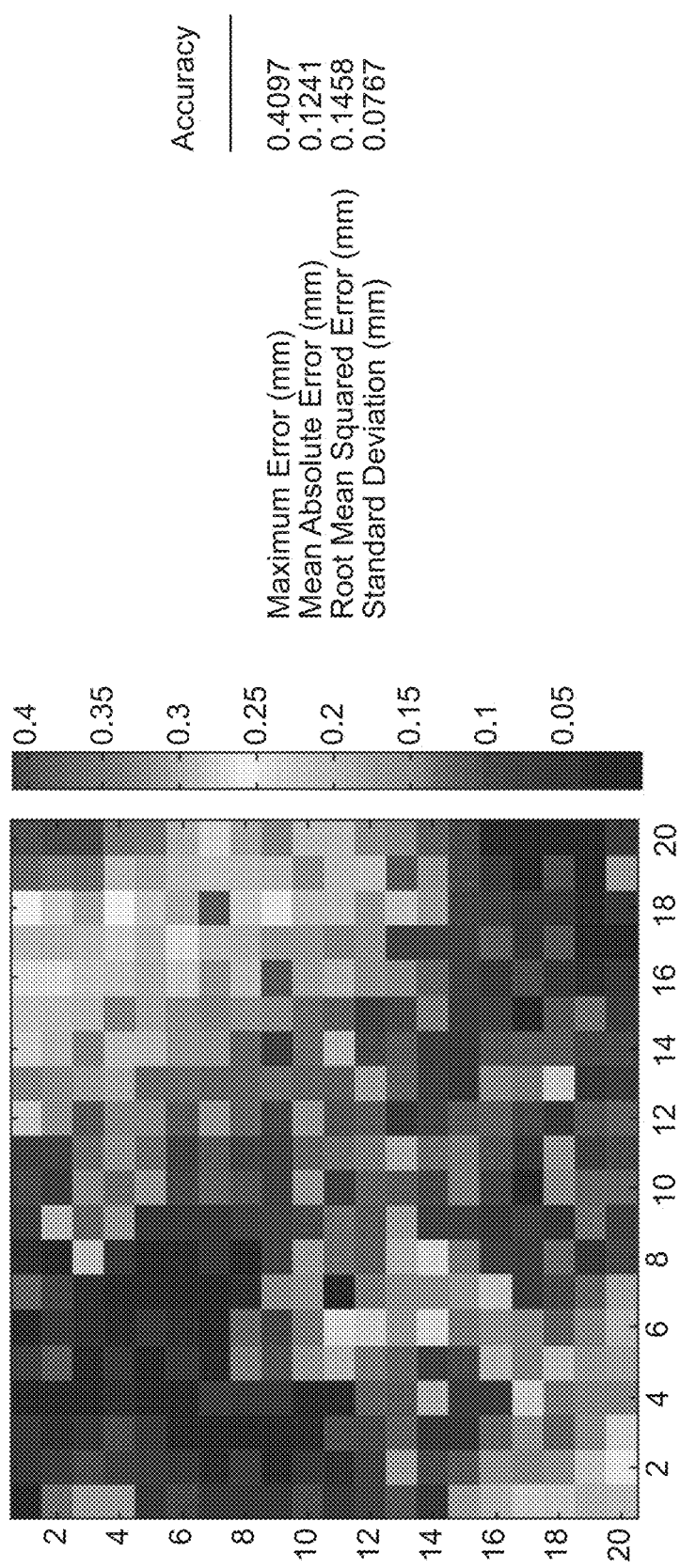
FIG. 16 depicts the accuracy in different parts of the field of view in an exemplary simulation of embodiments of the present invention.

FIG. 16 depicts the accuracy in different parts of the field of view for a system according to various embodiments. The error, values and deviation can be used to characterize the data over time.

Figure 17:
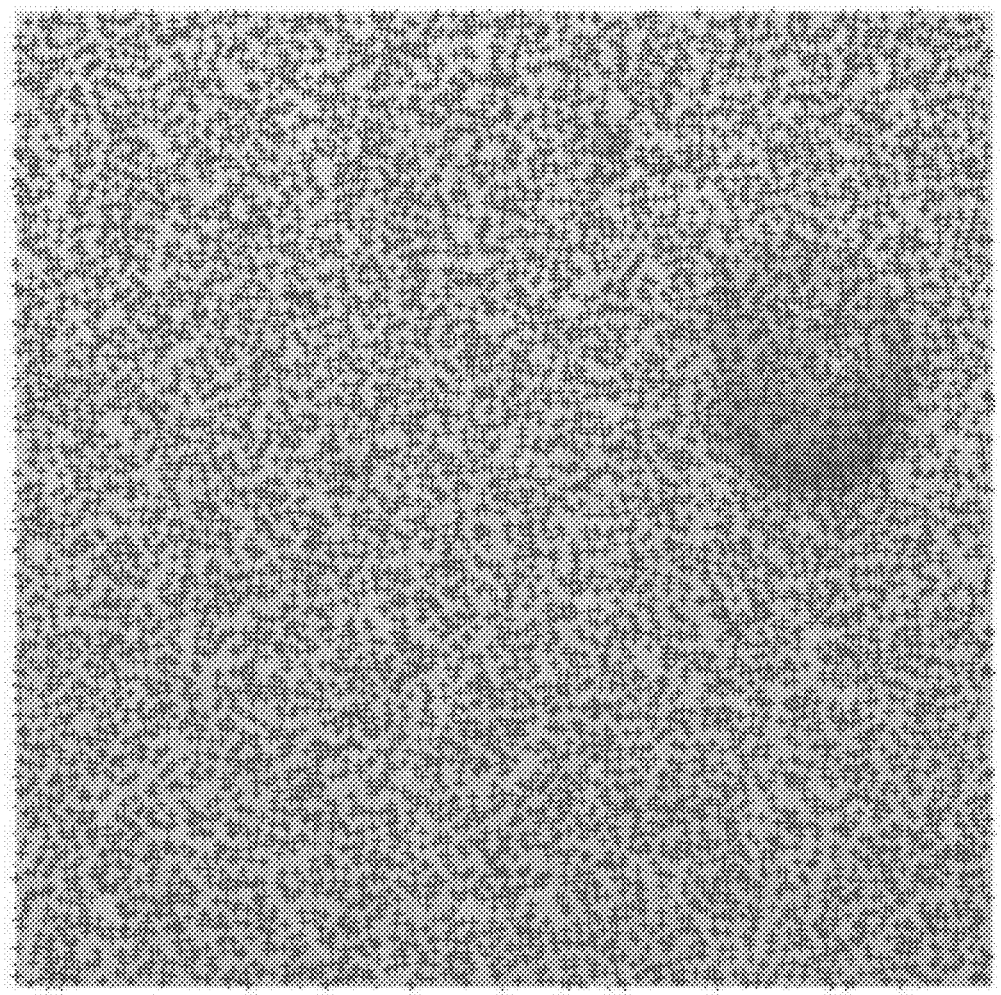
FIG. 17 illustrates an example of a visible light image overlaid with algorithmically generated points of interest according to preferred embodiments.
Figure 18:
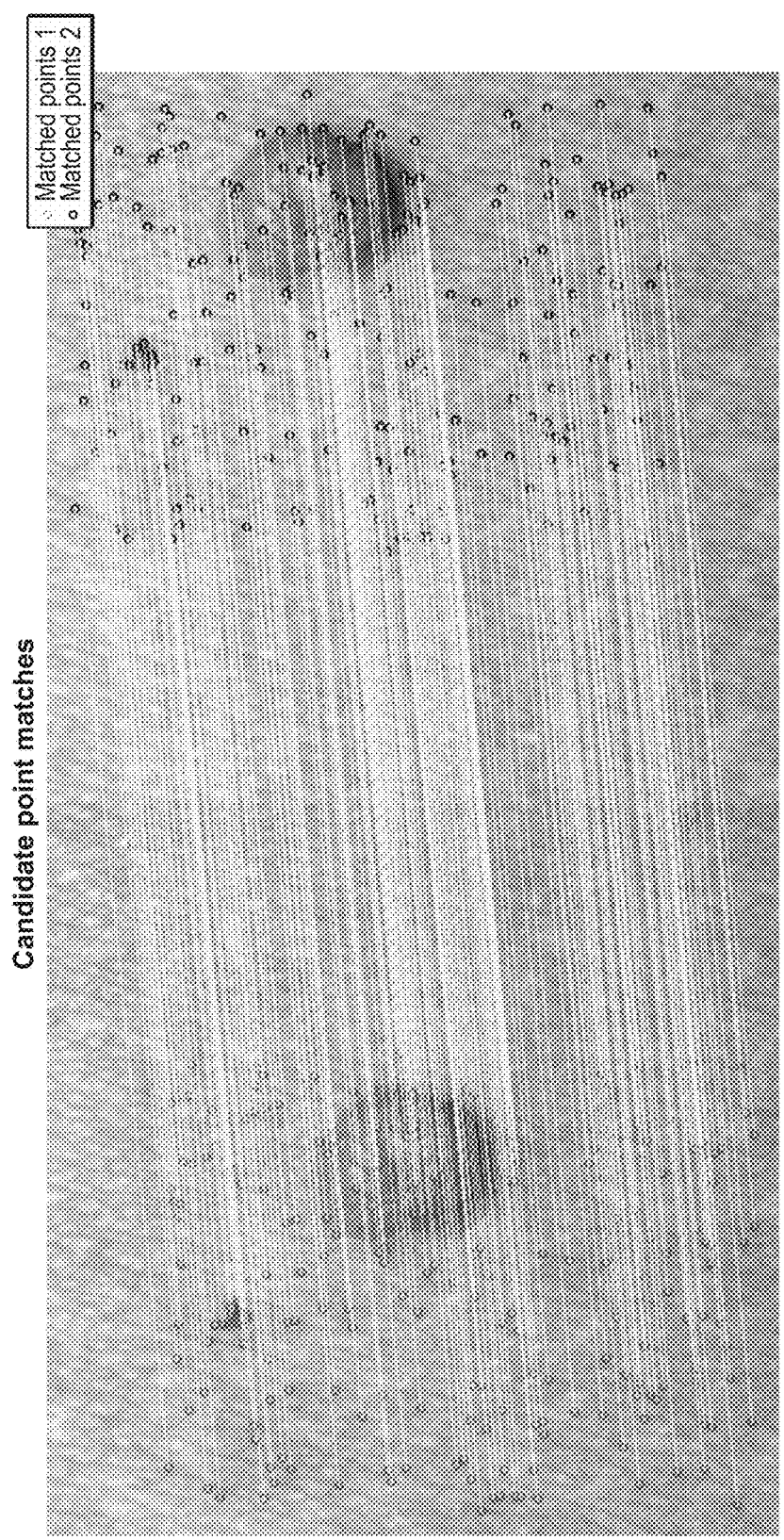
FIG. 18 illustrates an example of co-registration of algorithmically identified points of interest in two related images taken under different conditions according to preferred embodiments.
Figure 19:
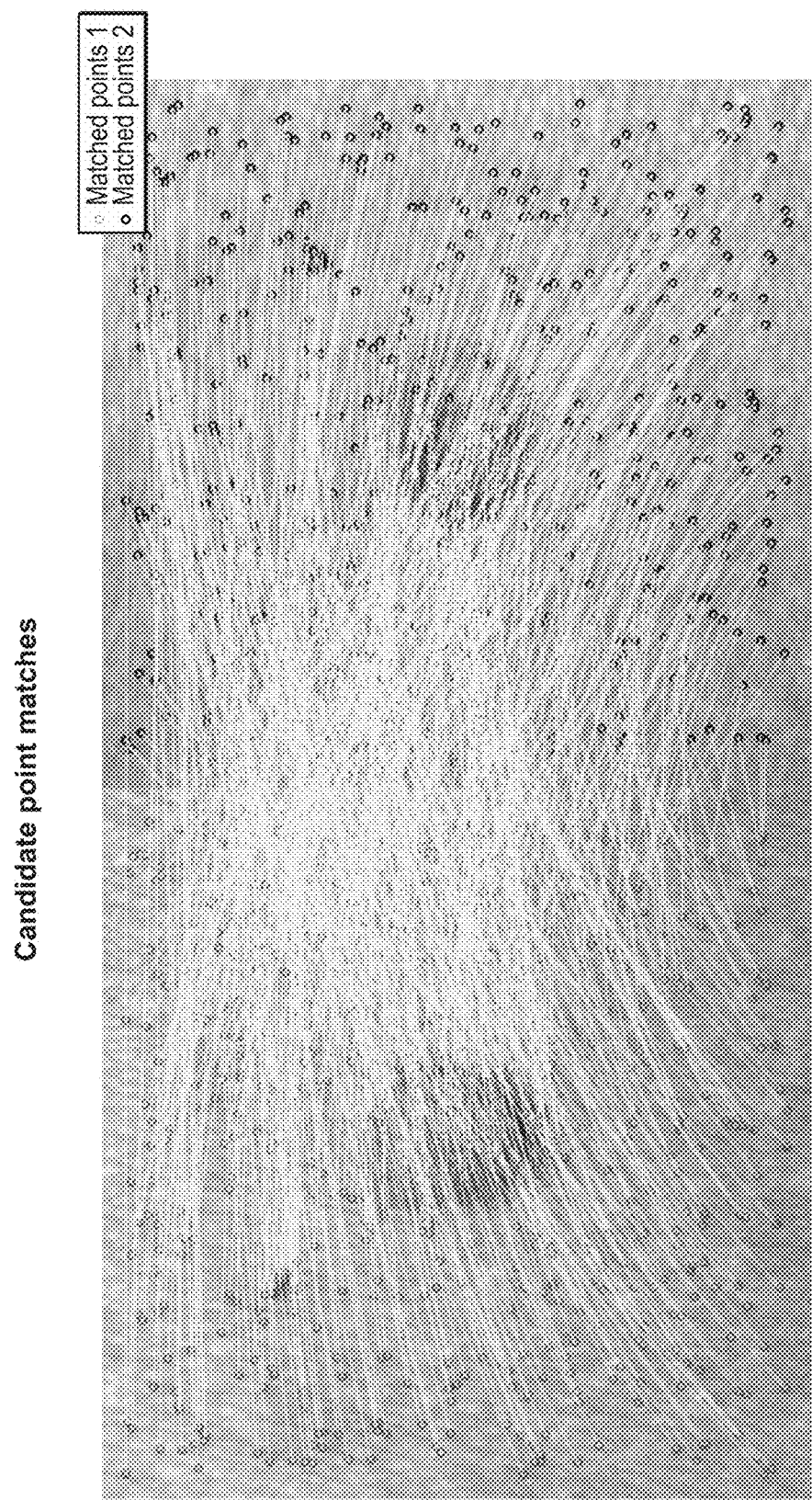
FIGS. 19 and 20 illustrate the robustness of an exemplary algorithm in accordance with the present invention in being able to identify and co-register points on different images that have been rotated, flipped, or skewed.
Figure 20:
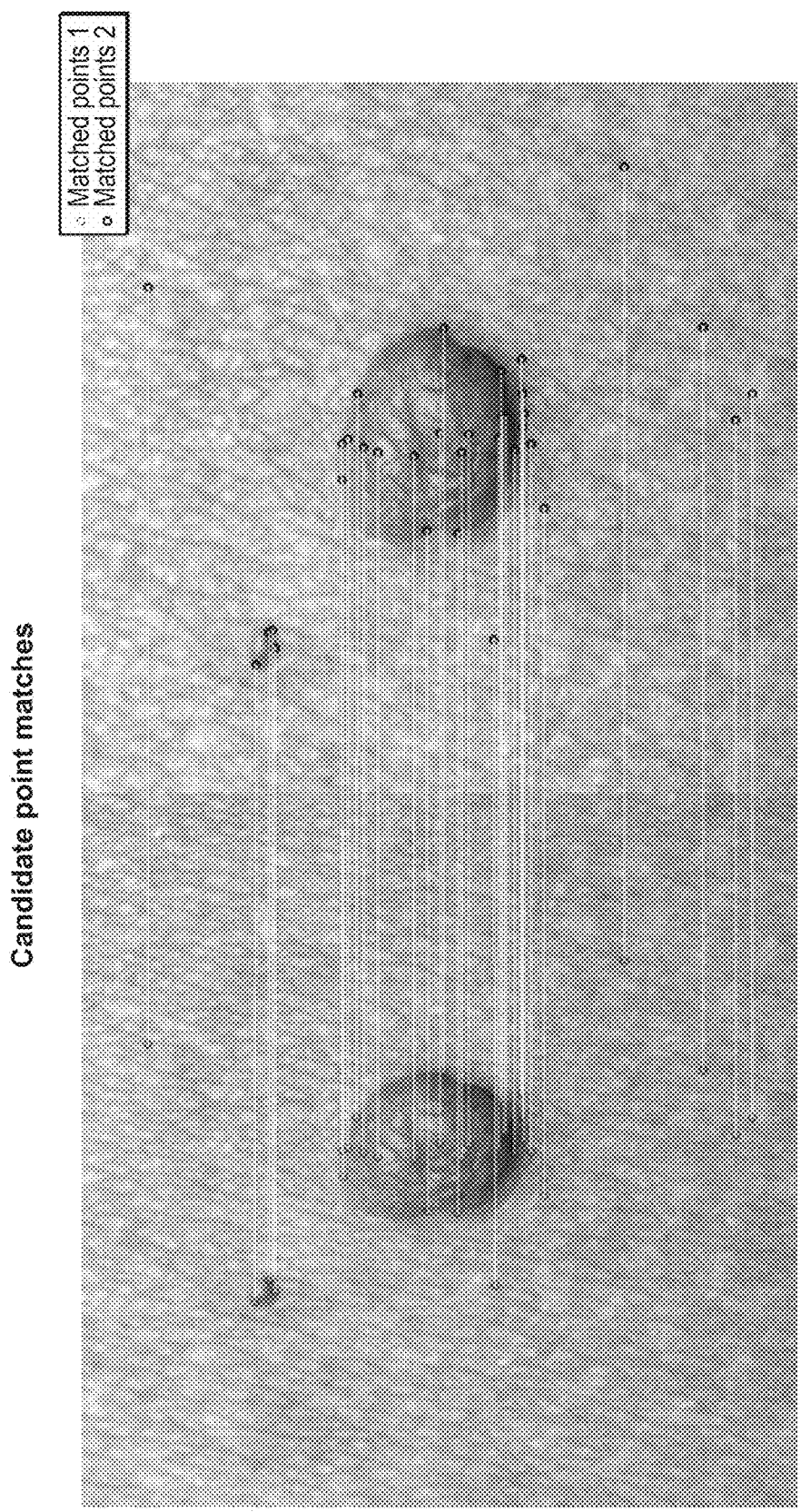

FIG. 17 illustrates an example of a visible light image overlaid with algorithmically generated points of interest according to various embodiments. FIG. 18 illustrates an example of co-registration of algorithmically identified points of interest in two related images taken under different conditions. FIGS. 19 and 20 illustrate the robustness of the algorithm in being able to identify and co-register points on different images that have been rotated or flipped. Such robustness is crucial to reliably link images under less-than-ideal conditions when the device may be moved between acquisitions.

Figure 21:
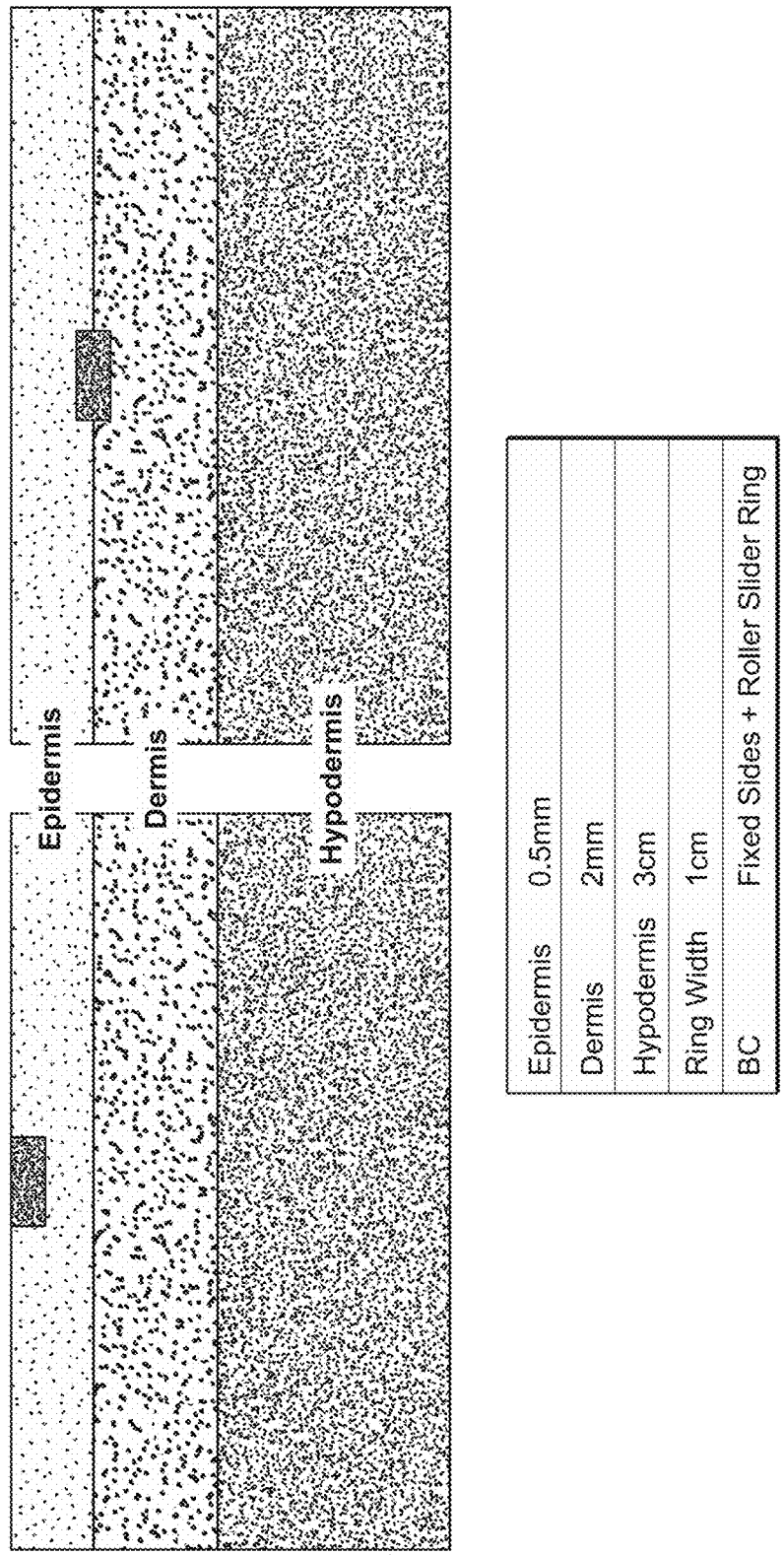
FIG. 21 illustrates virtual phantoms used to validate exemplary reconstruction algorithms and determine exemplary device parameters using finite element analysis (FEA) techniques.

FIG. 21 illustrates virtual phantoms used to validate the reconstruction algorithms and determine optimal device parameters using finite element analysis (FEA) techniques. Variants on the phantoms include those with lesions at the surface (epidermis) and those with lesions on the border between the epidermis and dermis. Examples of measurements performed on tissue phantoms can be found in Wortman, T. D., Hsu, F., Slocum, A. H. (2016), "A Novel Phantom Tissue Model for Skin Elasticity Quantification," Journal of Medical Devices, 10(2), p. 020961, the entire contents of which is incorporated herein by reference. Thus, preferred embodiments utilize phantoms made from synthetic materials and/or materials derived from natural sources. Such phantoms can be fabricated from materials such as Agar, polydimethyloxane (PDMS), titanium oxide, epoxy resins, porcine skin gelatin, collagen, light scattering particles and polyacrylamide gels, for example. The phantom can include at least three different layers, such as the epidermis, dermis, and hypodermis layers with thicknesses selected to emulate different conditions found frequently at different locations on the body. Lesions can also be fabricated in the synthetic phantoms to emulate different depths at which a lesion can extend above and/or below the dermis. These phantoms can be used for calibration of each measurement of tissue stiffness as described in the present application to aid in the diagnosis of disease such as skin cancer. Note that the individual layers of the phantom, as well as an embedded lesion, can have separately measured stiffness values to enable calibration of the diagnostic tissue stiffness measurements described herein.

In some embodiments, displacements in tissue with and without lesions can be modeled to optimize device parameters. A full-factorial parametric finite element analysis (FEA) study was performed with 3000 design points using a bottom elastic boundary condition and with the lesion placed in the epidermal-dermal junction. Evaluated variables included epidermis thickness, dermis thickness, hypodermis thickness, lesion thickness, lesion diameter, diameter of area of applied vacuum, and vacuum pressure. The evaluated output was the center deformation, which is equivalent to the maximum deformation.

Stepwise regression was performed on the results. Vacuum diameter and pressure were the variables with the highest sensitivity. Lesion diameter as well as epidermal and hypodermal thickness were also important. Dermis and lesion thickness were not important.

Figure 22:
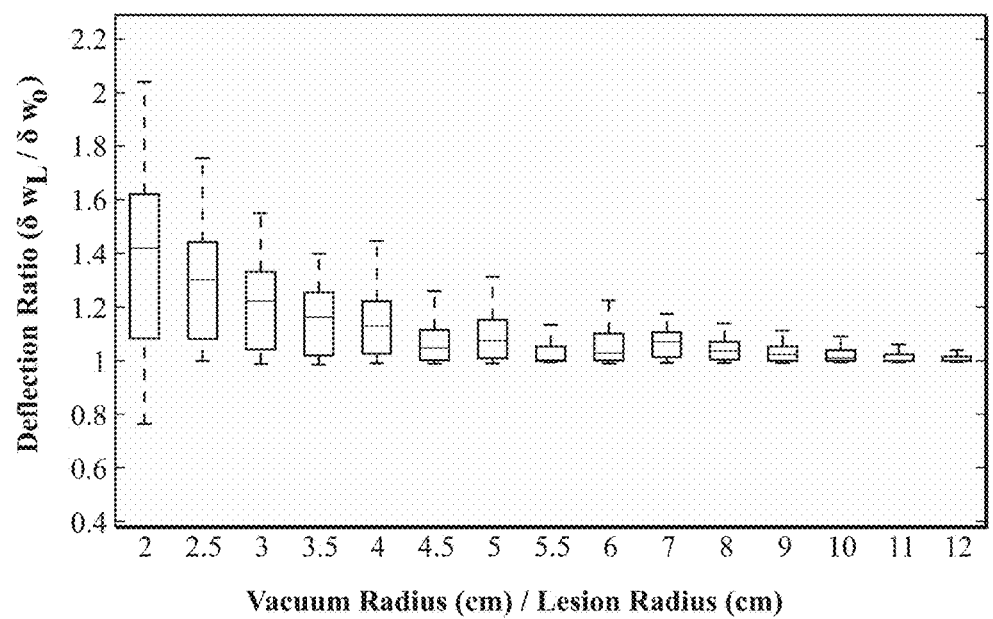
FIG. 22 illustrates simulated displacement results in non dimensional form for an exemplary embodiment.

FIG. 22 is a plot of the lesion deflection ratio to the vacuum-lesion ratio. Lesion deflection ratio is the non-dimensionalized amount of displacement of a lesion to the amount of displacement without a lesion. Maximizing this amount will help to ensure that a cancerous lesion is differentiated from healthy tissue. As shown in FIG. 22, the lesion deflection ratio is greatest when the negative pressure area is close to the same size of the lesion.

Figure 23A:
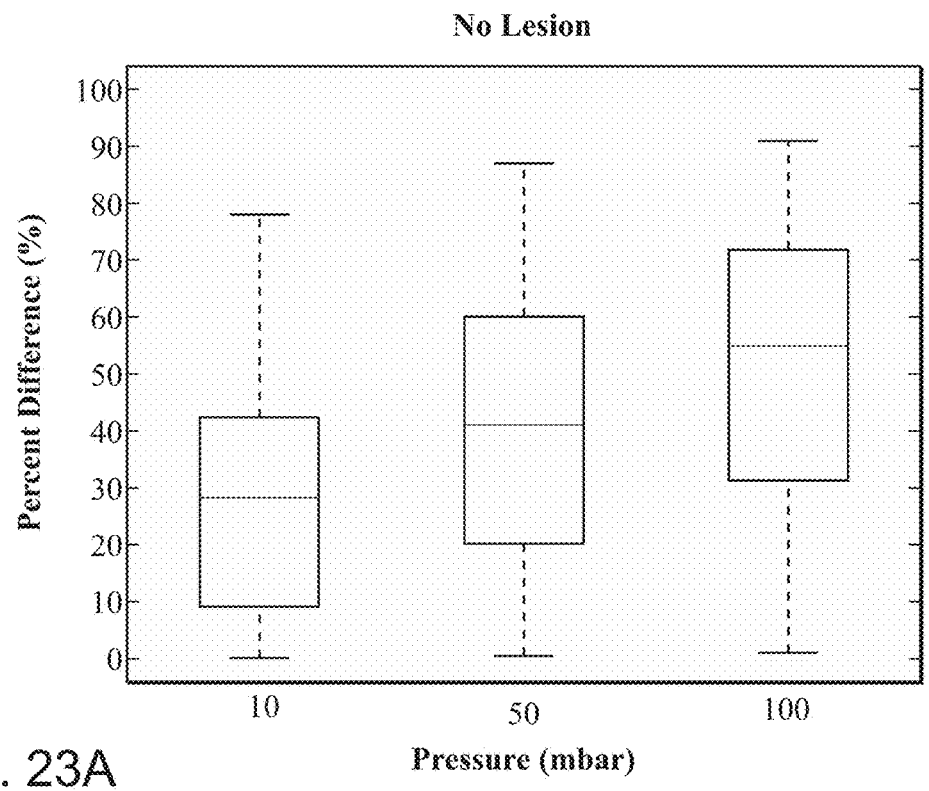
FIGS. 23A and 23B illustrates an evaluation of a linear approximation model against a finite element analysis model for different pressures in a simulated tissue measurement without a lesion and with a lesion, respectively, for an exemplary embodiment.
Figure 23B:
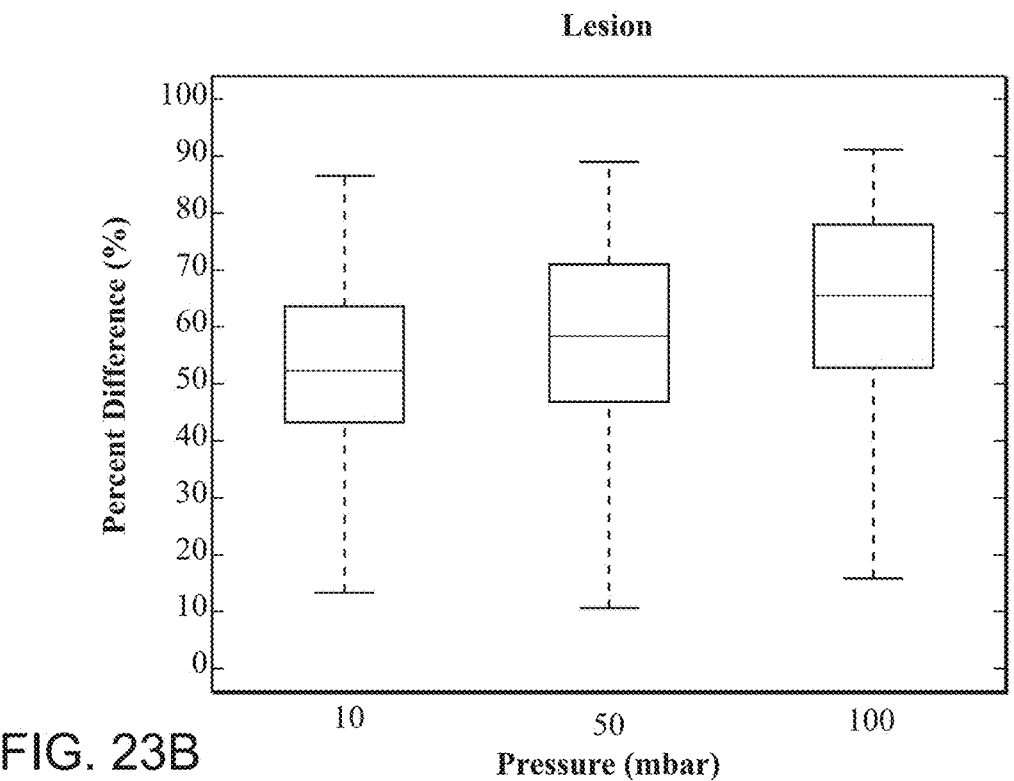
Figure 24A:
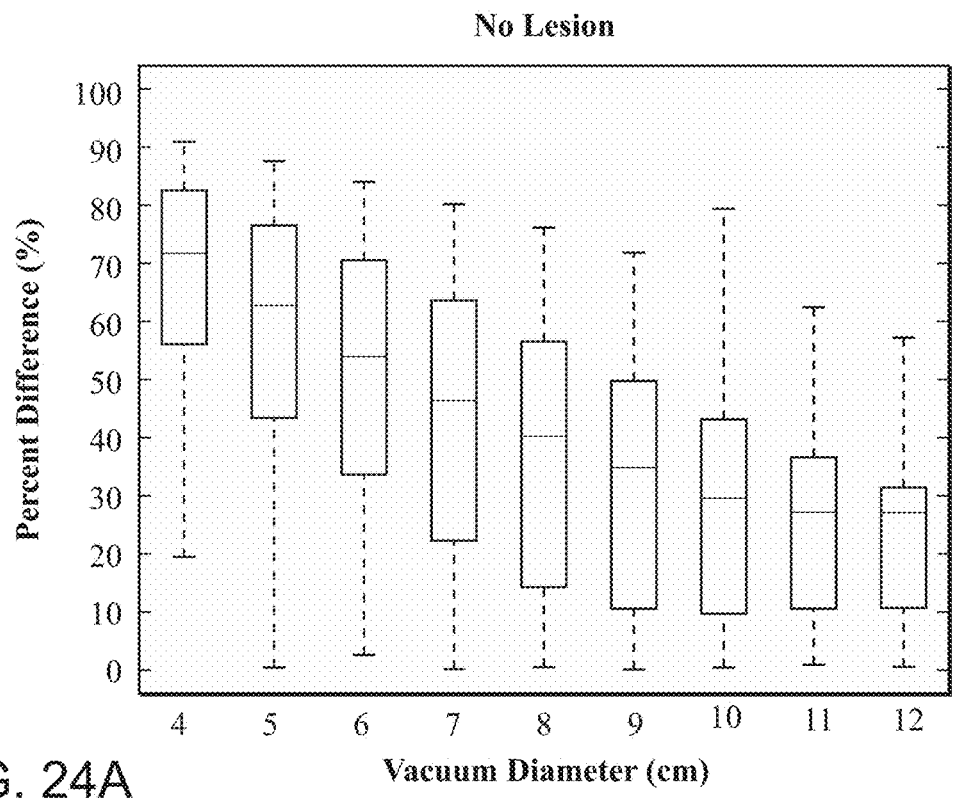
FIGS. 24A and 24B illustrates an evaluation of a linear approximation model against a finite element analysis model for different areas of application in a simulated tissue measurement without a lesion and with a lesion, respectively, for an exemplary embodiment.
Figure 24B:
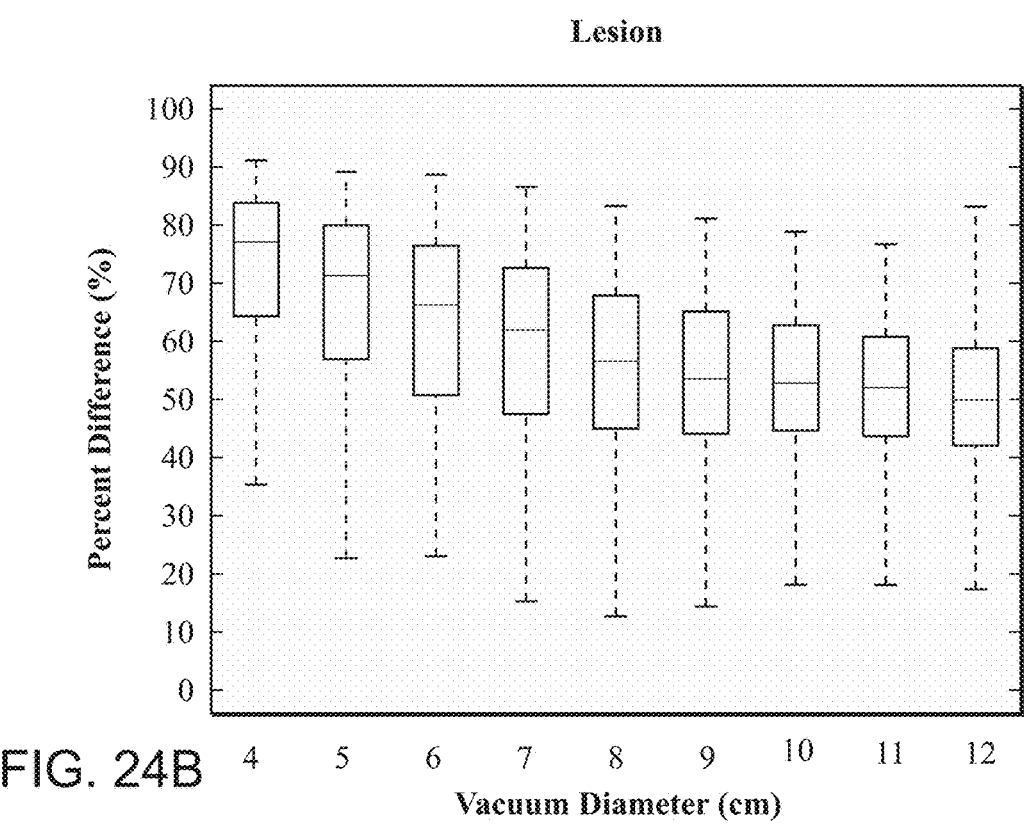

The full-factorial parametric study was also used to evaluate a linear first-order multi-layer approximation equation describing the tissue deformation. The maximum deflection was calculated for each design point using the linear equation. The results were compared to the FEA results. FIGS. 23A and 23B show how the linear model deviates from the FEA results for different pressures for models without a lesion and with a lesion, respectively. FIGS. 24A and 24B show how the linear model deviates from the FEA results for different vacuum diameters for models without a lesion and with a lesion, respectively.

As expected, when pressure increases, the maximum deflection also increases. Large deflections are non-linear, so the FEA results deviate further from the linear approximation equation. The linear model is also less accurate for smaller vacuum diameters. This is caused by the boundary condition effects. This validates the quality of the approximation for small deflections; however the error will become significant for large deflections.

The presence of melanin in the dermis is the most significant sign of melanoma but cannot be used as the sole diagnosis criterion because the earliest stage of melanoma, in situ, is located only in the epidermis. Other signs of melanoma are the thickening of collagen fibers in papillary dermis (fibrosis), increased blood supply at the lesion periphery (erythematic reaction), and lack of blood within the lesion in the areas destroyed by cancer. All of these indications result in detectable changes within the properties of the skin. Understanding the composition of healthy skin and how its properties change when cancer develops can be critical when trying to detect cancer in its earliest stages.

As stated previously, human skin made up of 3 layers. It is useful to understand the important characteristics of each layer as they help define the overall properties of the skin. The epidermis is a layer of partially keratinized cells that progressively dehydrate as they migrate to outer surface. This thin layer provides a tough barrier to the external environment. The dermis is a network of elastic collagen fibers and lymphatic elements that contributes the most to stiffness as it acts as a place of resistance for external stress. Collagen is a long, fibrous protein that provides structure in tissues. The hypodermis is a viscous and soft layer composed of fat that acts as a cushion. The layer thickness is approximately 50 μm for the epidermis, 1 mm for the dermis, and the hypodermis varies from 1 mm to 5 cm. The thickness of each layer, as well as the skin's elastic properties, vary significantly based on several factors, including age, body site, and hydration.

Skin properties are quite complicated: skin is non-linear, anisotropic, inhomogeneous, evolves over time, and has inconsistent boundary conditions. Langer's lines can be useful in describing the patterns of biomechanical anisotropy. These lines are topological lines that can be drawn on the human body to map the natural orientation of collagen fibers in the dermis. Along these lines, the skin has the least flexibility and the highest stiffness.

The mechanical properties of skin are some of the most useful tissue characteristics that can aid in medical diagnosis of various conditions. Cancer causes noticeable variations in the elastic properties or thickness of tissue. Palpation of hard masses is a primary screening technique for several types of malignant tumors including breast, thyroid, and prostate. Manual palpation is commonly used by dermatologists to detect skin cancer by sensing changes in the stiffness of a tumor compared with its surrounding tissue. The variation in stiffness results in a larger Young's modulus for squamous cell carcinoma and malignant melanoma and a reduced Young's modulus for basal cell carcinoma.

In vivo estimation of the skin's Young's modulus, a measure of stiffness, shows a range of values covering four orders of magnitude ($10^4$ to $10^8$ Pa). A commonly recovered value is approximately 10 kPa, but the results are highly dependent on measurement method. The Young's modulus has been shown to decrease with age as the skin begins to lose its elastic properties. Cancer, on the other hand, increases the Young's Modulus. The average Young's Modulus of cancerous skin has been found to be 52 kPa based on measurements taken in vitro.

Different models have been used to estimate the Young's Modulus of the individual skin layers. The Young's Modulus of the epidermis, the thin layer of dehydrated skin cells, is typically found to be 1 MPa. The value for the dermis is much less, ranging from 35-300 kPa. The hypodermis, composed of mostly fat, is even lower, with values of 2-35 kPa.

Tissue stiffness is not static, but changes during different physiological processes. Examples include tissue development (aging), tissue remodeling during wound healing (scars), and tumor formation (cancer).

Cancerous tissue as a whole is stiffer than normal tissue; however, cancer cells themselves are actually more compliant than healthy cells. Individual cancer cells, independent of cancer type, are far less stiff than normal cells, due to the reorganization of the cell cytoskeleton or inner-cellular scaffolding. The ability of a cell to deform, flow, remodel, and contract allows metastasis as the cell can escape the tumor and migrate by way of the blood or lymph vessels to form tumors at multiple, distant sites. Cancer cells with the highest invasive potential can be five times less stiff than healthy cells.

Cancerous tissue becomes stiffer on a macroscopic scale because the extracellular matrix (ECM) or stroma remodels and stiffens so that the architecture and physical properties become fundamentally different. Part of the increase in stiffness can be attributed to excess activities of lysyl oxidase, which cross-links collagen fibers and other ECM components. Collagen metabolism is also deregulated in cancer, causing increased expression, elevated deposition, and altered organization. Collagen is the primary component contributing to the tensile strength of tissue. Increases in ECM stiffness enable cells to generate increased traction forces on their surroundings, which enhance growth, survival, and invasion to other parts of the body.

Melanoma can also be detected by observing variations in the blood supply to a lesion. A cancerous lesion has elevated metabolic activity and therefore requires increased blood supply to survive. The development of additional blood vessels facilitates an increased tumor mass. Blood vessel vascularization gradually increases during the transition process from benign nevi to dysplastic nevi to melanoma. Excessive vasculature is a clear indication of a high chance of malignancy.

Diagnostic technology may be quantified and compared using measures of sensitivity and specificity. Sensitivity, or the true positive case, is the probability that a patient tests positive for cancer and actually has cancer. Specificity, or the true negative case, is the probability that a patient tests negative for cancer and actually doesn't have cancer. Biopsy ratio is an important measure of specificity. Biopsy ratio is the number of biopsies of benign lesions to make a diagnosis of one skin cancer and this value varies from 5:1 to 500:1.

The ABCD acronym (Asymmetry, Border irregularity, Color Variation, Diameter) was developed to assist dermatologists in visual diagnosis. Subsequent to the acronym's development, E (elastography) was added to the list to remind physicians to look for evolving or changing lesions. Several other similar checklists have also been proposed that vary in complexity. The sensitivity and specificity for these visual checklist techniques ranges from 57-90% and 59-90%, respectively.

Different lighting conditions have been used to improve visual diagnosis by creating increased contrast between the lesion and healthy skin surrounding it. A Wood's lamp, similar to a black light, emits light in the UV spectrum (wavelength of ~360 nm). Melanin absorbs in this spectral range while collagen reflects it; the resulting contrast makes it easier to distinguish between the two.

All dermatologists use visual inspection to detect cancerous lesions; however, it has not proven to be very effective. One study found that $\frac{1}{3}^{rd}$ of melanomas were missed when diagnosis was attempted with simple visual inspection. Another study concluded that the diagnostic accuracy of dermatologists using only visual inspection is less than 70% with more experience leading to higher diagnostic accuracy. Visual diagnosis is commonly associated with a risk of false-negative diagnosis (missed melanomas) and false-positive diagnosis (unnecessary biopsies).

Elastography can be performed using acousto-optic methods by applying a small, low frequency dynamic acoustic force to the skin. An 8 Ω, 0.1 W speaker can be placed 1 cm from a lesion and driven with a 10 V peak-to-peak sine wave at 5 Hz. The area of interest can be illuminated at an off-axis angle of 40° with a collimated, coherent 5 mW, 543 nm DPSS laser. A CCD camera running at 200 Hz captures the laser reflections. The laser produces a speckle pattern on the skin and the combination of a misfocused lens and acoustic force induces a lateral motion of the speckle pattern. Local strain response can be quantified and encoded into a 2-D surface map by tracking the shift in the speckle pattern. The speckle shift image is further processed using a convolution filter to identify regions in the image that have different strain responses to applied dynamic force.

Because skin is a viscoelastic material, several variations in skin stiffness values can occur. Repeatedly stretching the skin, or pre-conditioning, alters the mechanical properties as the tissue takes time to recover to its original state. Posture can also affect the amount of slack in skin resulting in significant deviations in measured values. Measurements using torsional strain, suction cups, or speed of shear wave propagation are all influenced by posture.

One analog method can utilize a modified tonometer. A tonometer is a tool traditionally used by ophthalmologists to measure eye pressure. This tool measures the force required to produce a given deformity of tissue by using weight to drive a blunt piston into tissue and then measuring the tissue deformation. These tools are relatively cheap and very simple to use. Another analog method is an elastometer, which uses a constant-tension spring to distract two loci of skin and a strain gauge to determine the force applied.

A digital device example can be a tissue ultrasound palpation tool. This is a handheld probe with ultrasound transducer and an in-series load cell. The load cell is used to determine the applied force when the measurement is taken.

Preferred embodiments provide multiple skin cancer detection techniques in a handheld form factor that is cost effective and can be used by a consumer. The device also performs automation of visual analysis and manual human palpation producing greater sensitivity and consistency. Manual human palpation cannot easily detect very small changes or anomalies of the skin. These changes must be so large compared to normal skin tissue that the difference can be detected by the touch of a finger. Automation enables greater sensitivity to allow changes to be detected immediately. This results in cancer being diagnosed sooner and a greater chance of survival.

As noted above, the enclosure's internal pressure may be applied in a number of ways and monitored and recorded using a pressure transducer. A PCB can connect the electronics to an external CPU for data I/O. In accordance with various embodiments, the device can be a portable hardware attachment for a handheld standalone device configured to perform a fully automated sequence of measurements and to process and store the data.

When analyzing tissue, the device can record a sequence of visible light and structured light images as the pressure is varied. Each image may have a corresponding pressure transducer measurement. A tissue mechanics model can then be used to calculate tissue stiffness based on the applied force and measured displacement. A normalized compliance map may be generated and overlaid onto the visible light images. Additional information such as size, color, and texture can be measured from the visible light images to further describe tissue characteristics. Image processing of a lesion in standard practice typically measures the ABCD's—Asymmetry, Border Irregularity, Color, and Diameter. An image-processing algorithm of the present invention can quantify these metrics. Once the measured characteristics and stiffness are quantified, the data can be used with a machine learning neural network to give an instantaneous score of the probability that the lesion is cancerous. Furthermore, the same lesion can be monitored daily, weekly, and/or monthly to allow evaluation of quantified metrics from each measurement as they change over time. Changing lesions are 400× more likely to be cancerous.

If a lesion is determined to be cancerous, the normalized compliance map can be used to determine the border extents of the lesion. This map provides a means to determine the extent of the lesion for excision. Lesion boundaries are projected on the lesion or the border can be directly printed or tattooed onto the tissue to provide the doctor with a path to properly remove the lesion.

The systems and devices of the present invention can be used to assess a variety of skin conditions. For example, assessment of the severity of edema employs similar palpation techniques to those previously described for cancer detection. An edema is caused by blocked or malfunctioning veins that allow fluid to leak into the interstitial space. The fluid-filled tissue has different mechanical properties than surrounding tissue including elasticity. The severity of an edema can be diagnosed by applying momentary pressure and evaluating the restoration of the skin to its original form before pressure was applied. Embodiments of the devices and methods described herein can be used to automatically apply a force to edematous tissue to cause displacement followed by observation of changes in tissue surface shape and displacement over time.

Figure 25:
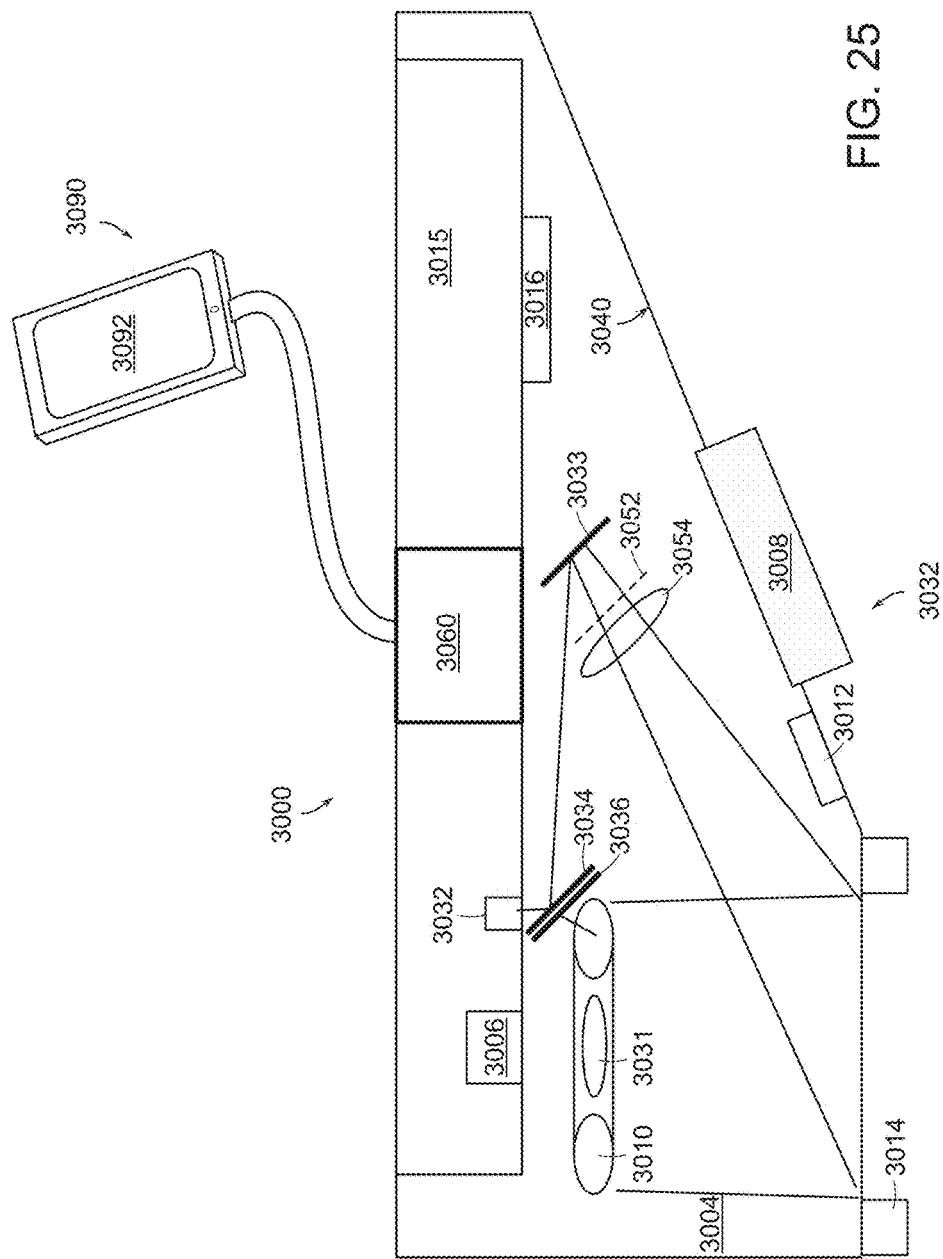
FIG. 25 depicts a standalone embodiment of the present invention that can interface with a computer or mobile communications device such as a smartphone.

FIG. 25 illustrates an embodiment of a tissue stiffness measurement system 3000 that includes a tissue stiffness measurement device that can use a communications module 3060 to communicate with a portable computing device 3090 including an external display, computer, or handheld wireless mobile communications device such as a smartphone or tablet computer. The portable computing device 3090 can have a touchscreen 3092 in some embodiments. The tissue measurement device 3000 can use the portable computing device 3090 to provide an interface for the user as well as for some processing and data storage capabilities. The device 3000 can include a camera 3006 and an LED 3032 or other light source to provide imaging and illumination capabilities. The device 3000 may be ergonomically shaped as a handle or grip 3040 to improve the ease of gripping by a user. To improve portability, the tissue displacement component of the device 3000 may be a button pump 3008 that can be operated manually by the hand of a user. However, the tissue displacement component can include mechanical linkages or other means of displacement as described above with reference to, for example, FIG. 6. In accordance with some embodiments, a seal 3014 can ensure that vacuum is maintained within the chamber 3004 of the device 3000. Custom driver circuitry 3016 can be used to operate the components of the device 3000. The device 3000 can include a battery 3015 to power components including the camera 3006, LED 3032, communications module 3060, a ring light 3010, or driver circuitry 3016. In some embodiments, port The device 3000 may include the ring light 3010 to evenly illuminate the tissue for visible light imagery that can then be associated with structured light images and also may be utilized for standard or spectroscopic image analysis. In some embodiments, the ring light 3010 may comprise a halo-shaped component that collects and re-emits the light from the LED 3032 to uniformly illuminate a tissue surface. The halo-shaped component may include frosted glass or plastic materials. If the camera 3006 of the device 3000 is not suitable to directly image a tissue surface, additional magnifying optics and polarization filters 3031 may be placed between the camera 3006 and the tissue surface.

Light from the LED 3032 may be shared between the ring light 3010 and the light path to the projector using a half-mirror 3034 and a liquid crystal device 3036. The liquid crystal 3036 can be used in part to determine the distribution of light among the paths. Light from the LED 3032 may also reflect from a mirror 3033 and pass through a mask 3052. In various embodiments, the mask 3052 can be a gobo or a DMD/DLP array. A focusing lens 3054 can focus the structured light from the mask 3052 onto a tissue surface.

In some embodiments, the communications module 3060 can provide a wired or wireless connection between the device 3000 and the external display, computer, or handheld mobile communication device. In accordance with various embodiments, the wireless connection can be BLUETOOTH™, 802.xx or wi-fi, near-field communication, or any other suitable wireless communication method. In some embodiments, the communications module 3060 can include a mini- or micro-USB connector or various proprietary digital ports.

In accordance with various embodiments, tissue measurement systems, devices, and methods taught herein can determine the absolute stiffness of a portion of tissue. In some embodiments, the determination of absolute stiffness can include the characteristic equation for bending of a plate on an elastic foundation (Equation 1):

$$D\nabla^4 w + Fw = P \qquad (1)$$

$$D = \frac{Eh^3}{12(1-v^2)} \qquad (2)$$

where D is the flexural rigidity, w is the vertical displacement, F is the foundation modulus, P is the uniform pressure, E is the elastic modulus, h is the thickness, and v is the Poisson ratio. Similar analyses are described in a publication by CB Dolicanin et al. (Dolicanin, C. B., V. B. Nikolic, and D. C. Dolicanin. "Application of finite difference method to study of the phenomenon in the theory of thin plates." Scientific Publications of the State University of Novi Pazar Series A: Appl. Math. Inform. And Mech, vol. 2, 1 (2010): 29-43), the entire contents of which is incorporated herein by reference in its entirety.

In some embodiments, processing of the data can include determining the vertical displacement of the tissue using an analysis of multiple structured light images as described above. Because the process relies on differential pressure and displacement, the result of the analysis is, for example, five different associated pressures and displacement matrices (i.e., an array of XYZ location information for each of the dots of the structured light pattern) if six different images are used. In some embodiments, systems and devices taught herein can take two of the sets of known pressure (P) and measured deflection array (w) and solve for D and F in Equation 1 by loosely coupling the equations and applying a finite difference matrix. In some embodiments, deflection measurements at the lowest value of pressure can be used to negate non-linear effects such that D and F remain the same. By applying this technique, two equations can be developed:

$$(DL+F)w_1 = P_1 \qquad (3)$$

$$(DL+F)w_2 = P_2 \qquad (4)$$

where L is a finite difference matrix. By weakly coupling the equations and iterating solutions for D and F, an estimate of the stiffness parameters may be obtained.

In some embodiments, techniques described herein can provide absolute measures of stiffness or components of stiffness including flexural rigidity (proportional to elastic modulus of the top layer of skin, i.e., epidermis) or foundation modulus (which is effectively the elastic modulus of the dermal and hypodermal layers). By differentiating the stiffness of the epidermal layer and the dermal/hypodermal layers, additional information can be identified such as depth of a lesion below the surface. In effect, a pseudo-3D representation of stiffness can be created in some embodiments using the camera, light source, and mechanical stimulus.

Figure 26:
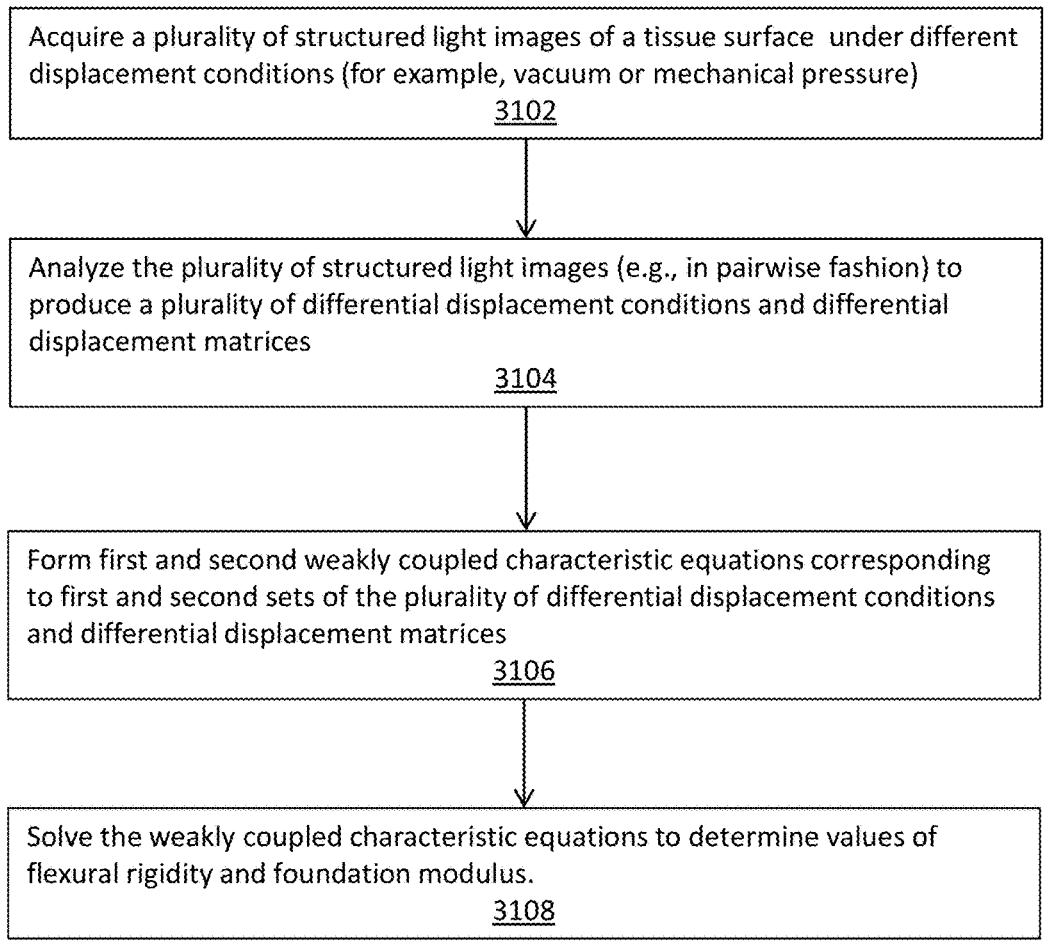
FIG. 26 describes a method of determining absolute tissue stiffness according to preferred embodiments.

FIG. 26 describes a method of determining absolute tissue stiffness according to preferred embodiments. The method can include acquiring a plurality of structured light images of a tissue surface under different displacement conditions (step 3102). In some embodiments, the displacement conditions can be brought about through vacuum pressure or mechanical pressure. The method also includes analyzing the plurality of structured light images to produce a plurality of differential displacement conditions and differential displacement matrices (step 3104). In some embodiments, the analysis can be conducted on the plurality of structured light images in pairwise fashion. The method also includes forming first and second weakly coupled characteristic equations corresponding to first and second sets of the plurality of differential displacement conditions and differential displacement matrices (step 3106). The method further includes solving the weakly coupled characteristic equations to determine values of flexural rigidity and foundation modulus (step 3108).

In some embodiments, tissue stiffness measurements systems, devices, and methods taught herein can include a dot ordering algorithm that operates using geometrical constraints of the system and physical tissue parameters such as the continuous tissue surface, minimal occlusions, and low spatial frequency. As shown in FIG. 27A, the camera 3210 can be oriented with respect to a surface 3220 at an angle $\alpha$. In some embodiments, the angle $\alpha$ can be 45°. Due to the orientation and position of the projector relative to the camera, the structured light pattern 3230 on the flat surface 3220 as viewed by the camera 3210 can be shaped like a trapezoid.

Figure 27B:
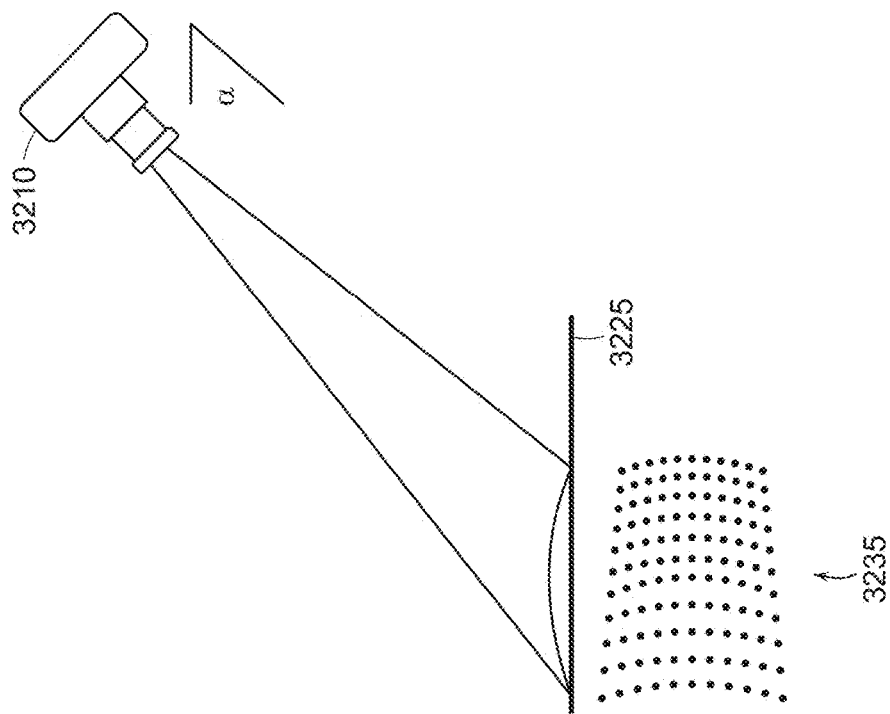
FIG. 27B depicts the geometry of a camera relative to a curved surface and the resulting structured light pattern viewed by the camera in accordance with some embodiments of the present invention.
Figure 27A:
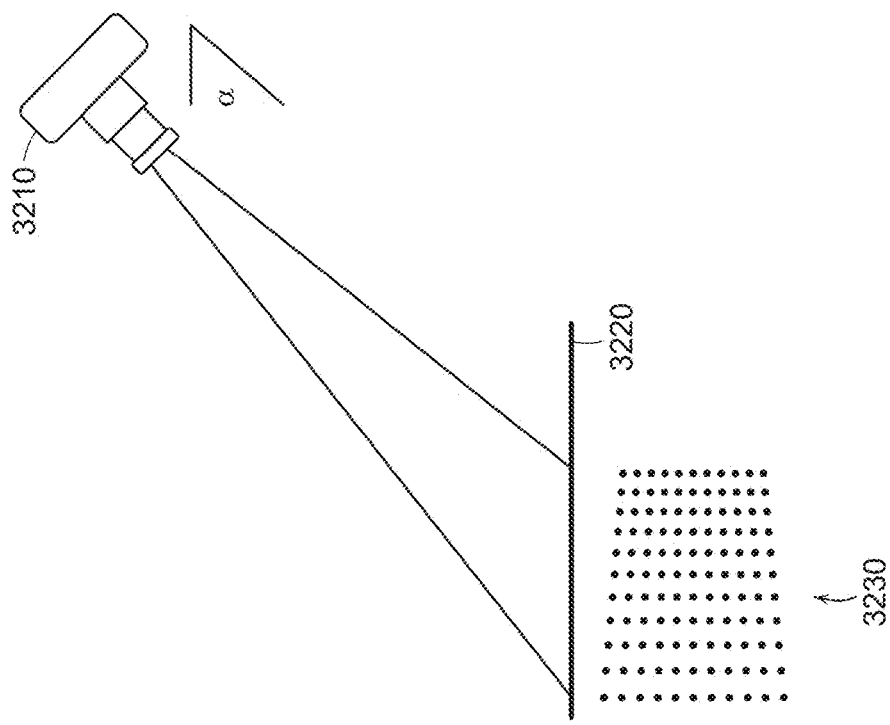
FIG. 27A depicts the geometry of a camera relative to a flat surface and the resulting structured light pattern viewed by the camera in accordance with some embodiments of the present invention.

As shown in FIG. 27B, the structured light pattern 3235 as viewed by the camera 3210 on a curved surface 3225 can be different than the structured light pattern 3230 on the flat surface 3220. Specifically, some of the light dots in the structured light pattern 3235 on the curved surface 3235 can be translated in the horizontal direction with respect to the expected position of those dots on in the structured light pattern 3230 on the flat surface 3220. Because the camera 3210 is at an angle $\alpha$, every unit change in height/displacement from the flat surface (e.g., the Z direction) can create a change in the lateral direction (e.g., the X direction). When angle $\alpha$ is 45°, the change in height and the change in lateral direction correspond in a 1:1 ratio. In addition, this change correspondence is an approximation that is degrades proportionally to how far the dot is from the center of the projection pattern. In the image obtained by the camera 3210 of the structured light pattern 3235 on the highly curved surface 3225, the dot pattern can be highly distorted due to a combination of a trapezoid/keystone effect and large height differences between neighboring dots. As a result, a change in height (e.g., the Z direction) can cause neighboring dots to both move up/down (e.g., in the Y direction) and left/right (e.g., in the X direction). Consequently, ordering and association of the dots in the structured light pattern image 3235 with the original dot pattern can be difficult.

Figure 28:
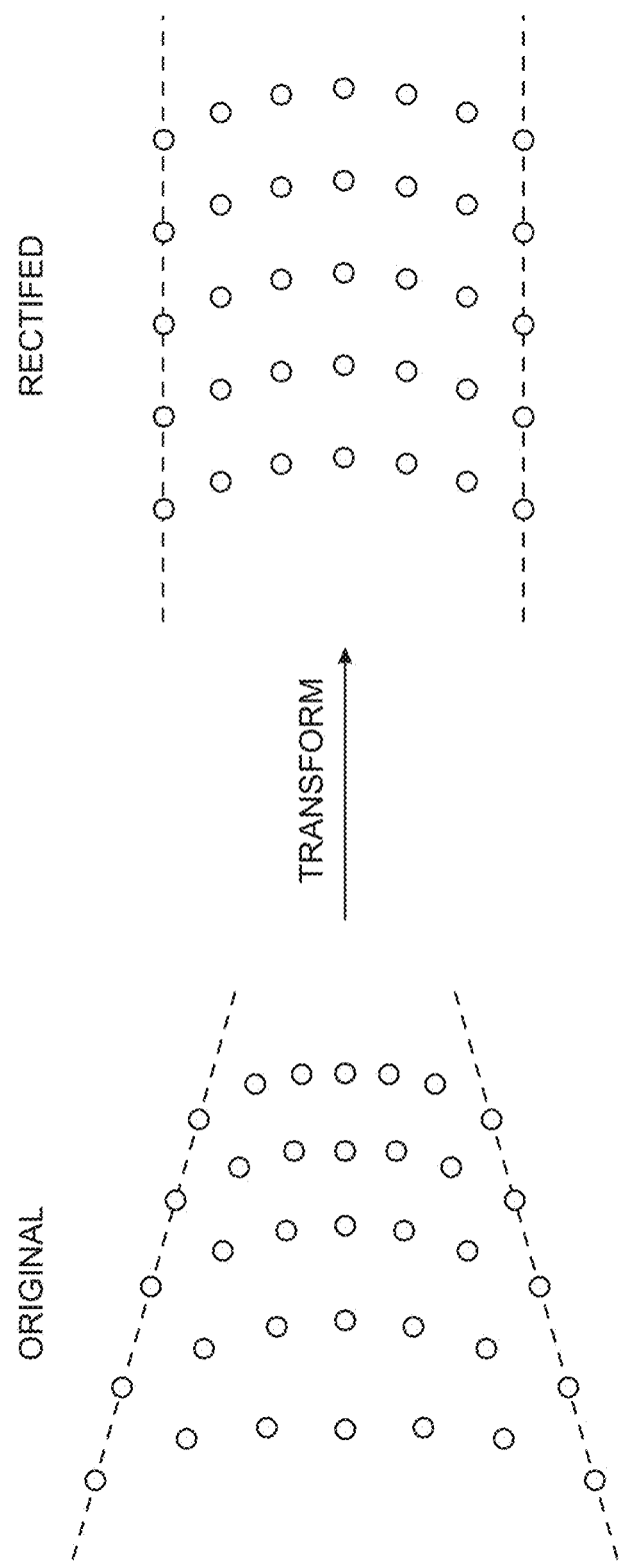
FIG. 28 depicts the results of a transformation to correct for surface curvature in accordance with some embodiments of the present invention.

To mitigate this issue, systems, devices, and methods for tissue stiffness measurement taught herein can transform the image from the camera so that dots that are along a horizontal line in the original dot pattern appear as horizontal in the camera image. This type of transformation is often called warping or rectification and is illustrated in FIG. 28. In some embodiments, a standardized transformation function can be applied to all images. In the transformed or rectified image, dots in the structured light pattern that are at different heights on the surface (e.g., in the Z direction) are only translated laterally (e.g., in the X direction) with respect to the original dot pattern such that lines of the dots remain horizontal. By rectifying the image, dots in the transformed image can be ordered more easily by the algorithm as the algorithm can scan along horizontal lines. In some embodiments, the transformation or rectification can be undone after the dots have been ordered by the algorithm. For example, the image can be warped back to its original shape and the original process can resume. The projection matrix can be applied to the 2D coordinates to transform them into 3D coordinates giving the surface profile.

While the present invention has been described herein in conjunction with preferred embodiments, a person of ordinary skill in the art can effect changes, substitutions or equivalents to the systems and methods described herein, which are intended to fall within the appended claims and any equivalents thereof.

What is claimed is:

1. A tissue stiffness measurement device, comprising:
a light source that generates light;
a light pattern optical system that couples the light from the light source to form a structured light pattern on a three-dimensional tissue surface;
at least one imaging device that images the three-dimensional tissue surface, the at least one imaging device generating image data of the structured light pattern on the three-dimensional tissue surface;
a tissue modifying element that displaces the three-dimensional tissue surface such that a characteristic of the structured light pattern is modified; and
a data processor connected to a memory that receives light pattern image data from the at least one imaging device, the data processor computing tissue stiffness data of the three-dimensional tissue surface from processed light pattern image data.

2. The device of claim 1 wherein the light pattern optical system includes a mask or a digital light projection device, such that the structured light pattern is a dot pattern formed on the three-dimensional tissue surface.

3. The device of claim 2, wherein the data processor is configured to rectify an image of the illuminated three-dimensional tissue surface by placing a portion of dots in the dot pattern formed on the tissue surface on a horizontal line in the image.

4. The device of claim 1 wherein the light source comprises a laser.

5. The device of claim 1 wherein the light source emits one or more wavelengths to produce a visible light image of a tissue lesion.

6. The device of claim 5 wherein the light source comprises a light emitting diode.

7. The device of claim 5 wherein the light source comprises a ring emitter.

8. The device of claim 1 wherein the memory stores a machine learning neural network.

9. The device of claim 8 wherein the data processor is configured to analyze an image of a surface lesion obtained by the imaging device to determine one or more metrics of the surface lesion, the one or more metrics including tissue displacement data.

10. The device of claim 9 wherein the machine learning neural network compares the one or more metrics of the surface lesion to reference data stored in the memory to produce a likelihood score.

11. The device of claim 9, wherein the data processor is configured to:
generate a profile based on elements from a three-dimensional representation of the tissue surface and the one or more metrics;
compare the generated profile to database values stored in the memory; and
generate a score correlated to a likelihood that the tissue surface includes cancerous tissue.

12. The device of claim 1 wherein the data processor and memory are components of a handheld portable computer device that comprises a smartphone.

13. The device of claim 12, wherein the handheld portable computing device includes a display.

14. The device of claim 1 wherein the tissue modifying element includes a vacuum chamber and a vacuum source.

15. The device of claim 14 further comprising a pressure transducer.

16. The device of claim 14 wherein the vacuum source is at least one of a ball pump, a button pump, or a vacuum pump.

17. The device of claim 14 wherein the vacuum source operates in a range between 0 and 100 mbar.

18. The device of claim 14 wherein a diameter of the vacuum chamber is in a range from 2 to 12 cm.

19. The device of claim 1 wherein the tissue modifying element includes a flexure-based kinematic linkage force applicator.

20. The device of claim 1 wherein the tissue modifying element applies a dynamic or oscillatory force.

21. The device of claim 1 wherein the at least one imaging device comprises a first imaging device and a second imaging device, wherein a first image of a lesion is acquired by the first imaging device and a second image of the lesion is acquired by the second imaging device.

22. The device of claim 21 wherein the data processor computes a stereoscopic 3-D representation of the lesion from the first image and the second image.

23. The device of claim 1 wherein the tissue modifying element applies one or more of a normal force, a radial force, and a torsional force to an area of interest.

24. The device of claim 1 further comprising a source of UV and IR light and wherein the at least one imaging device is adapted to image at least one of UV or IR light from the three-dimensional tissue surface.

25. The device of claim 1, wherein the tissue modifying element applies a first displacement to the three-dimensional tissue surface while a first image is acquired and applies a second displacement of different magnitude or direction while a second image is acquired.

26. The device of claim 1, further comprising a housing in which the light source, light pattern optical system, and imaging device are mounted, the housing having a weight of less than 2 kilograms.

27. The device of claim 1, further comprising a sensor that measures tissue displacement.

28. The device of claim 1, wherein the data processor is configured to generate a quantitative stiffness map based on measured stiffness.

29. The device of claim 1 wherein the light pattern optical system further comprises a light patterning device.

30. The device of claim 29 wherein the light patterning device comprises a mask or a digital light patterning device that is configured to receive instructions defining one of a plurality of selectable light patterns to be directed onto the tissue surface.

31. A tissue stiffness measurement device, comprising:
a light source that generates light;
a light pattern optical system that couples the light from the light source to a three-dimensional tissue surface having a surface lesion;
at least one imaging device that images the three-dimensional tissue surface, the at least one imaging device generating image data of a surface pattern on the three-dimensional tissue surface;
a tissue modifying element that displaces the three-dimensional tissue surface such that a characteristic of the surface pattern is modified; and
a data processor connected to a memory that receives surface pattern image data from the at least one imaging device, the data processor computing tissue stiffness data of the surface lesion from processed surface pattern image data.

32. The device of claim 31 wherein the processed surface pattern image data includes tissue features.

33. The device of claim 31 wherein the data processor is configured to analyze the surface pattern image data including the surface lesion obtained by the imaging device to determine one or more metrics of the surface lesion, the one or more metrics including tissue displacement data.

34. The device of claim 33 wherein the memory stores a machine learning neural network that compares the one or more metrics of the lesion to reference data stored in the memory to produce a likelihood score.

35. The device of claim 31 wherein the at least one imaging device comprises a first imaging device and a second imaging device, wherein a first image of the surface lesion is acquired by the first imaging device and a second image of the surface lesion is acquired by the second imaging device.

36. The device of claim 35 wherein the data processor computes a stereoscopic 3-D representation of the surface lesion from the first image and the second image.

37. The device of claim 31 wherein the data processor is configured to identify points of interest in an image of a tissue surface.

38. The device of claim 31 wherein the data processor is configured to record in the memory at least one of a surface lesion boundary and vascularization of the surface lesion.

39. The device of claim 31 wherein the light pattern optical system further comprises a light patterning device.

40. The device of claim 39 wherein the light patterning device comprises a mask or a digital light patterning device.

41. The device of claim 31 wherein the tissue modifying element applies a force to the three-dimensional tissue surface to displace the three-dimensional tissue surface and wherein the at least one imaging device generates a plurality of images of the three-dimensional tissue surface at a plurality of different positions.

* * * * *